United States Patent
Slusher et al.

(10) Patent No.: US 11,191,732 B2
(45) Date of Patent: Dec. 7, 2021

(54) GLUTAMINASE INHIBITOR DISCOVERY AND NANOPARTICLE-ENHANCED DELIVERY FOR CANCER THERAPY

(71) Applicant: The Johns Hopkins University, Baltimore, MD (US)

(72) Inventors: Barbara S. Slusher, Baltimore, MD (US); Anne Le, Baltimore, MD (US); Takashi Tsukamoto, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/853,276

(22) Filed: Apr. 20, 2020

(65) Prior Publication Data
US 2020/0246274 A1   Aug. 6, 2020

Related U.S. Application Data

(62) Division of application No. 15/324,835, filed as application No. PCT/US2015/039579 on Jul. 8, 2015, now Pat. No. 10,660,861.

(60) Provisional application No. 62/022,523, filed on Jul. 9, 2014.

(51) Int. Cl.
| | |
|---|---|
| *C07D 417/12* | (2006.01) |
| *C07D 417/14* | (2006.01) |
| *C07D 285/135* | (2006.01) |
| *A61K 9/51* | (2006.01) |
| *A61K 9/00* | (2006.01) |
| *A61K 31/433* | (2006.01) |
| *A61K 45/06* | (2006.01) |
| *A61K 31/337* | (2006.01) |

(52) U.S. Cl.
CPC .......... *A61K 9/5153* (2013.01); *A61K 9/0019* (2013.01); *A61K 9/5146* (2013.01); *A61K 31/337* (2013.01); *A61K 31/433* (2013.01); *A61K 45/06* (2013.01); *C07D 285/135* (2013.01); *C07D 417/12* (2013.01); *C07D 417/14* (2013.01)

(58) Field of Classification Search
CPC . C07D 285/135; C07D 417/12; C07D 417/14
See application file for complete search history.

(56) References Cited

U.S. PATENT DOCUMENTS

| | | | |
|---|---|---|---|
| 8,420,123 B2 | 4/2013 | Troiano | |
| 9,687,563 B2 | 6/2017 | Chen | |
| 2006/0009431 A1 | 1/2006 | Earl | |
| 2013/0157998 A1* | 6/2013 | Li | C07D 417/06 514/210.18 |
| 2014/0005379 A1 | 1/2014 | Gu | |
| 2014/0142146 A1 | 5/2014 | Lemieux | |

FOREIGN PATENT DOCUMENTS

| | | |
|---|---|---|
| WO | 2013078123 | 5/2013 |
| WO | 2013090804 | 6/2013 |
| WO | 2014078645 | 5/2014 |
| WO | 2014089048 | 6/2014 |
| WO | 2015031059 | 3/2015 |
| WO | 2015101957 | 7/2015 |

OTHER PUBLICATIONS

Antczak, et al., "A new acivin prodrug designed for tumor-targeted delivery" Bioorganic& Medicinal Chemistry, 9:2843-2848 (2001).
Author Not Listed "Why is pancreatic cancer so hard to treat? Stroma provides new clues", Science Daily, 5 pages (2017).
Beletsi, et al., "Biodistribution properties of nanoparticles based on mixtures of PLGA with PLGA-PEG diblock copolmers", (2005).
Birnbaum, et al., "Genome profiling of pancreatic adenocarcinoma", Genes Chromosomes Cancer, 50(6):456-65 (2011).
Blackwood, et al., "Combination drug scheduling defines a "window of opportunity" for chemopotentiation of gemcitabine by an orally bioavailable, selective ChK1 inhibitor, GNE-900", Mol Cancer Therap, 12(10):1968-80 (2013).
Bryant, et al., "KRAS. feeding pancreatic cancer proliferation", Trends Biochem Sci. 39(2): 91-100 (2014).
DeLaBarre, et al., "Full-length human glutaminase in complex with an allosteric inhibitor", Biochemistry, 50(50):10764-70 (2011).
dl Magliano, et al., "Roles for KRAS in pancreatic tumor development and progression", Gastroenterology. 144(6):1220-9 (2013).
Dimou, et al., "Overcoming the stromal barrier: technologies to optimize drug delivery in pancreatic cancer", Ther Adv Med Oncol., 4(5):271-9 (2012).
Ensign, et al., "Mucus-penetrating nanoparticles for vaginal drug delivery protect against herpes simplex virus", Sci Trans Med, 4: 138ra79 (2012).
Feig, et al., "The pancreas cancer microenvironment", Clin Cancer Res., 18(16):4266-76 (2012).

(Continued)

*Primary Examiner* — Noble E Jarrell
(74) *Attorney, Agent, or Firm* — Pabst Patent Group LLP

(57) ABSTRACT

Currently available glutaminase inhibitors are generally poorly soluble, metabolically unstable, and/or require high doses, which together reduce their efficacy and therapeutic index. These can be formulated into nanoparticles and delivered safely and effectively for treatment of pancreatic cancer and other glutamine addicted cancers. Studies demonstrate that nanoparticle delivery of BPTES, relative to use of BPTES alone, can be safely administered and provides dramatically improved tumor drug exposure, resulting in greater efficacy. GLS inhibitors can be administered in higher concentrations with sub-100 nm nanoparticles, since the nanoparticles package the drug into "soluble" colloidal nanoparticles, and the nanoparticles deliver higher drug exposure selectively to the tumors due to the enhanced permeability and retention (EPR) effect. These factors result in sustained drug levels above the IC50 within the tumors for days, providing significantly enhanced efficacy compared to unencapsulated drug.

11 Claims, 14 Drawing Sheets

(56) References Cited

OTHER PUBLICATIONS

Feldmann, et al., "An orally bioavailable small-molecule inhibitor of Hedgehog signaling inhibits tumor initiation and metastasis in pancreatic cancer", Mol Cancer Therap., 7(9):2725-35 (2008).
Gref, et al., "Stealth corona-core nanoparticles surface modified by polyethylene glycol (PEG): influences of the corona (PEG chain length and sudace density) and of the core composition on phagocytic uptake and plasma protein adsorption", Colloids Surf B. Biointerfaces, 18(3-4):301-13 (2000).
Gross, et al., "Antitumor activity of the glutaminase inhibitor CB-839 in triple-negative breast cancer", Molecular Cancer Therapeutics, 13(4):890-901 (2014).
Hak, et al., "The Effect of Nanoparticle Polyethylene Glycol Surface density on Ligand directed Tumor Targeting Studied in vivo by Dual Modality Imaging", ACS Nano, 6(6):5648-58 (2012).
Hariharan, et al., "Analysis of mortality rates for pancreatic cancer across the world". HPB Oxford, 10(1):58-62 (2008).
Hingorani, et al., "Trp53R 172H and KrasG 120 cooperate to promote chromosomal instability and widely metastatic pancreatic ductal adenocarcinoma in mice", Cancer Cell, 7(5):469-83 (2005).
Iacobuzio-Donahue, et al., "Genes/c basis of pancreas cancer development and progression: insights from whole-exome and whole-genome sequencing", Clin Cancer Res., 18(16):4257-65 (2012).
International Search Report for corresponding PCT application PCT/US2015/039579 dated Oct. 12, 2015.
Jones, et al., "Core signaling pathways in human pancreatic cancers revealed by global genomic analyses", Science, 321(5897):1801-6 (2008).
Keenan, et al., "A listeria vaccine and depletion of T-regulatory cells activate immunity against early stage pancreatic intraepithelial neoplasms and prolong survival of mice", Gastroenterology, 146(7):1784-94 e6 (2014).
Le, et al., "Glucose-independent glutamine metabolism via TCA c)/cling for proliferation and survival in B cells", Cell Metabolism, 15(1):110-21 (2012).
Liang, et al., "Complex roles of the stroma in the intrinsic resistance to gemcitabine in oancreatic cancer: where we are and where we are going", (2017).
Liu, et al., Global regulation of nucelotide biosynthetic genes by c-Myc, Pios One, 3(7):e2722 (2008).
Lukey, et al., "Therapeutic strategies impacting cancer cell glutamine metabolism", Future Med. Chem., 5(14):1685-1700 (2013).
Lyssiotis, et al., "Pancreatic cancers rely on a novel glutamine metabolism pathway to maintain redox balance", Cell Cycle, 12(13):1987-8 (2013).
Mosqueira, et al., "Biodistribution of long-circulating PEG-gra Ited nanocapsules in mice. Effects of PEG chain length and density", Pharma Res., 18(10):1411-19 (2001).
Nance, et al., "A dense poly(ethylene glycol) coating improves penetration of large polymeric nanoparticles within brain tissue", Sci Transl Med, 4(149):149ra119 (2012).
Pandian, et al., "PEG-PHB-glutaminase nanoparticle inhibits cancer ce4ll proliferation in vitro through glutamine deprivation", In Vitro Cell Dev Biol. Anim., 51(4):372-80 (2014).
Perry, et al., "PEGylated PRINT Nanoparticles. The Impact of PEG Density on Protein Binding, Macrophage Association, Biodistribution, and Pharmacokinetics", Nano Ltrs, 12(10):5304-10 (2012).
Reitzer, et al., "Evidence that glutamine, not sugar, is the major energy source for cultured HeLa cells", J Biol Chem, 254(8):2669-76 (1979).
Seltzer, et al., "Inhibition of glutaminase preferentially slows growth of glioma cells with mutant IDH1", Cancer Res, 70(22):8981-7 (2010).
Shukla, et al., "Design, Synthesis, and Pharmacological Evaluation of Bis-2-(5-phenylacetamido-1,2,4-thiadiazol-2-y!)ethyl Sulfide 3 (BPTES) Analogs as Glutaminase Inhibitors", J Med Chem, 55(23):10551-63 (2012).
Son, et al., "Glutamine supports pancreatic cancer growth through a KRAS-regulated metabolic pathway", Nature, 496(7443):101-5 (2013).
Thangavelu, et al., "Structural basis for the allosteric inhibitory mechanism of human kidney-type glutaminase (KGA) and its regulation by Raf-Mek-Erk signaling in cancer cell metabolism", PNAS, 109(20):7705-10 (2012).
Thomas, et al., "Kinetic characterization of ebselen, chelerythrine and apomorphine as giutaminase inhibitors", Biochem Biophysical Res Comm., 438(2):243-8 (2013).
Trott and Olson, "AutoDock Vina. improving the speed and accuracy of docking with a new scoring function, efficient optimization, and multithreading", J Comput Chem, 31(2):455-61 (2010).
Vila, et al., "Transport of PLA-PEG particles across the nasal mucosa, effect of particle size and PEG coating density", J Controlled Release, 98(2):231-244 (2004).
Von Hoff, et al., "Gemcitabine plus nab-paclitaxel is an active regimen in patients with advanced pancreatic cancer: a phase I/II trial", J Clin Oncology, 29(34):4548-54 (2011).
Walters, et al., "Clinical, molecular and genetic validation of a murine orthotopic xenografl modelof pancreatic adenocarcinoma using fresh human specimens",Plos One, 8(10):p.e77065 (2013).
Wang, et al., "Targeting mitochondrial glutaminase acitivty inhibits oncogenic transformation", Cancer Cell, 18(3):207-19 (2010).
Wise, et al., "Glutamine addiction: a new therapeutic target in cancer", Trends Biochem Sci., 35(8):427-33 (2010).
Wise, et al., "Myc regulates a transcriptional program that stimulates mitochondrial glutaminolysis and leads to glutamine addiction", PNAS, 105(48):18762-7 (2008).
Xu, et al., "Scalable method to produce biodegradeable nanparticles that rapidly penetrate human mucus", J. Controlled Release, 170(2):279-89 (2013).
Yabuuchi, et al., "Notch signaling pathway targeted therapy suppresses tumor progression and metastatic spread in pancreatic cancer", Cancer Ltrs, 335(1):41-51 (2013).

* cited by examiner

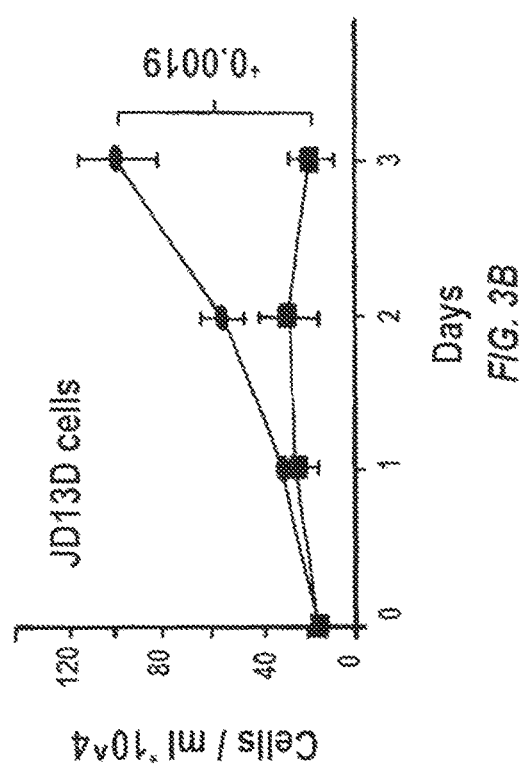
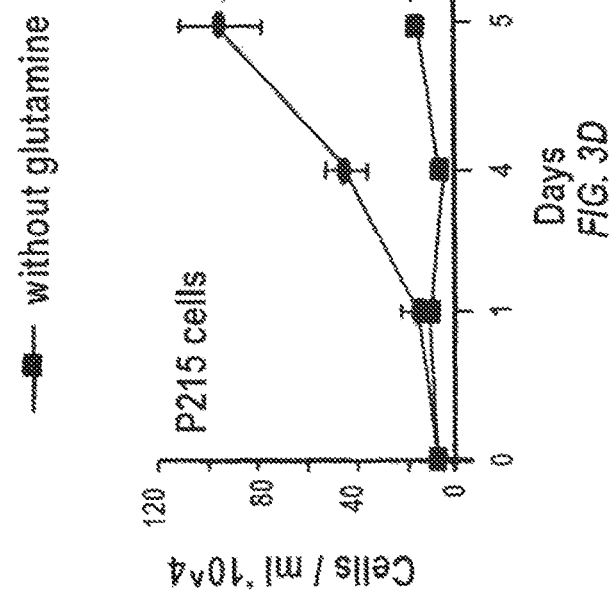
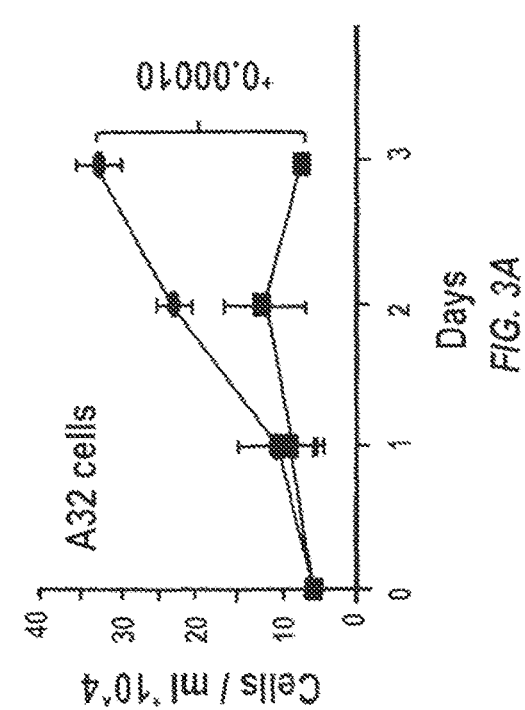
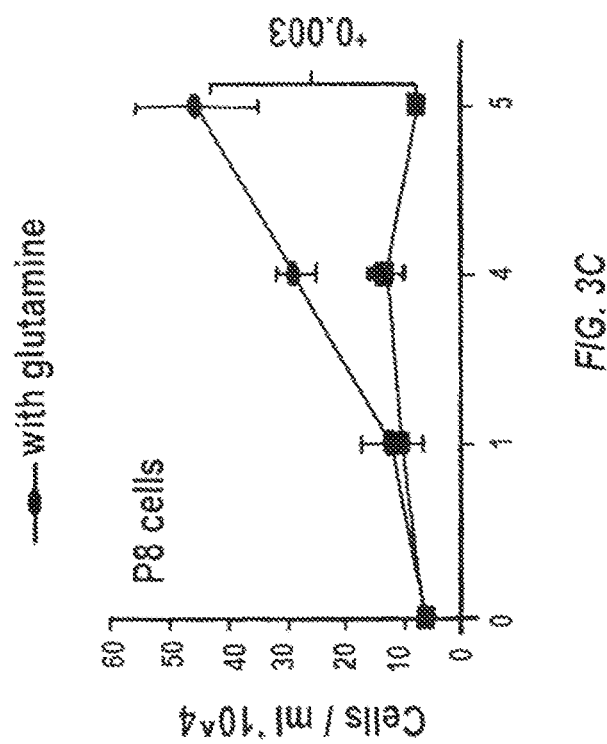

◆ 0 µM  ▲ 10 µM BPTES

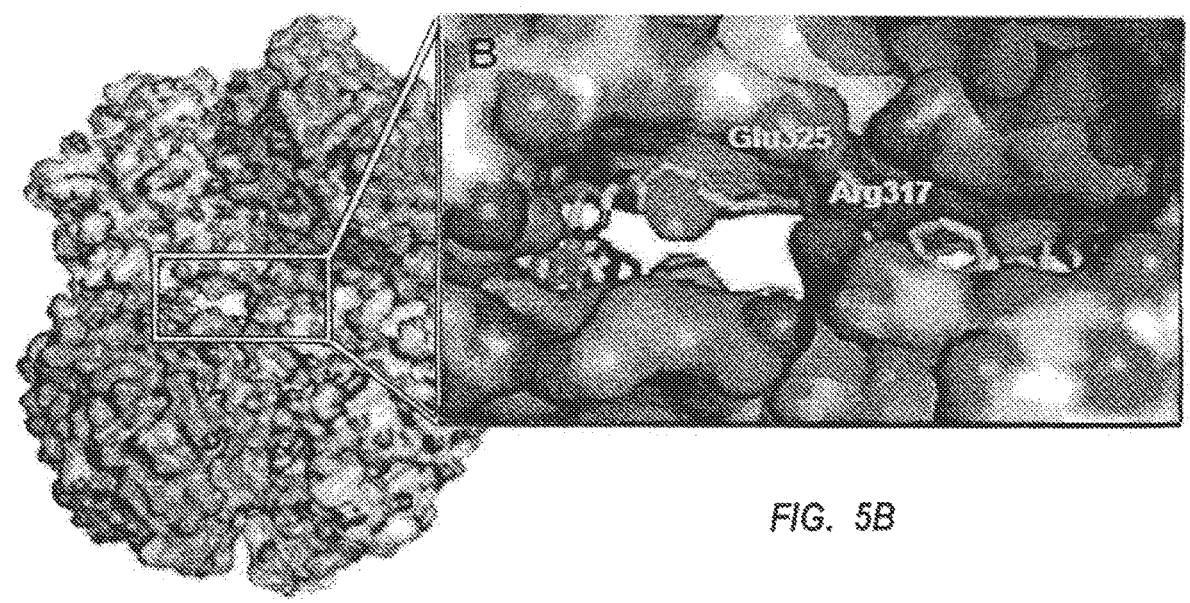
FIG. 5A
FIG. 5B
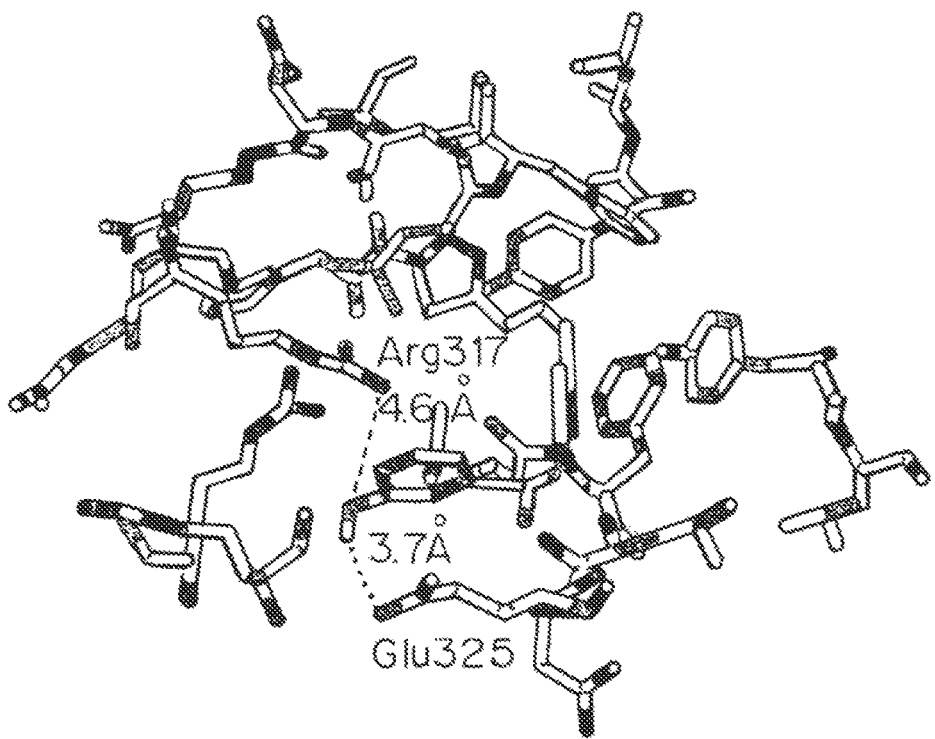
FIG. 6

GLUTAMINASE INHIBITOR DISCOVERY AND NANOPARTICLE-ENHANCED DELIVERY FOR CANCER THERAPY

CROSS-REFERENCE TO RELATED APPLICATIONS

This application is a divisional of pending prior U.S. application Ser. No. 15/324,835 filed Jan. 9, 2017, which is a National Phase application under 35 U.S.C. § 371 of International Application No. PCT/US2015/039579, filed Jul. 8, 2015, which claims priority to and benefit of U.S. Provisional Application No. 62/022,523, filed Jul. 9, 2014, the disclosures of which are hereby incorporated herein by reference in their entirety.

STATEMENT REGARDING FEDERALLY SPONSORED RESEARCH OR DEVELOPMENT

This invention was made with government support under grants CA169757, DA032470 and CA151838 awarded by the National Institutes of Health. The Government has certain rights in the invention.

BACKGROUND OF THE INVENTION

There were 46,420 estimated new cases and 39,590 deaths from pancreatic cancer in the United States in 2014. The incidence of carcinoma of the pancreas has markedly increased over the past several decades and ranks as the fourth leading cause of cancer death in the United States. (National Institutes of Health website). Despite the high mortality rate associated with pancreatic cancer, its etiology is poorly understood. Pancreatic cancer symptoms depend on the site of the tumor within the pancreas and the degree of tumor involvement.

The primary factors that influence prognosis are whether the tumor is localized and can be completely resected and whether the tumor has spread to lymph nodes or elsewhere. Exocrine pancreatic cancer is rarely curable and has an overall survival (OS) rate of less than 6%. The highest cure rate occurs if the tumor is truly localized to the pancreas; however, this stage of disease accounts for less than 20% of cases. For patients with localized disease and small cancers (<2 cm) with no lymph node metastases and no extension beyond the capsule of the pancreas, complete surgical resection is associated with an actuarial 5-year survival rate of 18% to 24%.

Surgical resection is the mainstay of curative treatment and provides a survival benefit in patients with small, localized pancreatic tumors. Patients with unresectable, metastatic, or recurrent disease are unlikely to benefit from surgical resection. Pancreatic tumors are resistant to treatment with chemotherapy and radiation. Surgical resection remains the primary modality when feasible; on occasion, resection can lead to long-term survival and provides effective palliation. The role of postoperative therapy (chemotherapy with or without chemoradiation therapy) in the management of pancreatic cancer remains controversial because much of the randomized clinical trial data available are statistically underpowered and provide conflicting results. (NIH website). Complete resection can yield 5-year survival rates of 18% to 24%, but ultimate control remains poor because of the high incidence of both local and distant tumor recurrence. Several phase III trials examined the potential overall survival (OS) benefit of postoperative adjuvant 5-FU-based chemoradiation therapy:

The Gastrointestinal Study Group (GITSG), a small randomized trial conducted by the GITSG in 1985 compared surgery alone with surgery followed by chemoradiation, reported a significant but modest improvement in median-term and long-term survival over resection alone with postoperative bolus 5-FU and regional split-course radiation given at a dose of 40 Gy. Charité Onkologie (CONKO)-001, a multicenter phase III trial of 368 patients with resected pancreatic cancer who were randomly assigned to receive six cycles of adjuvant gemcitabine, showed gemcitabine compared with observation alone yielded improved survival rates at 5 years of 20.7% for the gemcitabine arm versus 10.4% for the observation-alone arm and at 10 years the survival rates were 12.2% for the gemcitabine arm versus 7.7% for the observation-alone arm. The ESPAC-3 (NCT00058201) trial randomly assigned 1,088 patients who had undergone complete macroscopic resection to either 6 months of 5-FU (425 mg/m2) and leucovorin (20 mg/m2) on days 1 to 5 every 28 days or 6 months of gemcitabine (1,000 mg/m2) on days 1, 8, and 15 every 28 days. Median OS was 23.0 months (95% CI, 21.1-25.0) for patients treated with 5-FU plus leucovorin and 23.6 months (95% CI, 21.4-26.4) for those treated with gemcitabine (HR=0.94; 95% CI, 0.81-1.08; P=0.39).

The National Institutes of Health has stated that additional trials are still warranted to determine more effective adjuvant therapy for this disease.

Treatment options under clinical evaluation include the following:
Gemcitabine and capecitabine (ESPAC-4).
Gemcitabine and erlotinib (CONKO-005).
Gemcitabine and erlotinib with or without 5-FU/capecitabine-based chemoradiation (RTOG-0848).
Platinum analog or fluoropyrimidine versus single-agent gemcitabine: Many phase III studies have evaluated a combination regimen with either a platinum analog (cisplatin or oxaliplatin) or fluoropyrimidine versus single-agent gemcitabine.

Not one of these phase III trials has demonstrated a statistically significant advantage favoring the use of combination chemotherapy in the first-line treatment of metastatic pancreatic cancer.

In summary, pancreatic cancer often has a poor prognosis, even when diagnosed early. Pancreatic cancer typically spreads rapidly and is seldom detected in its early stages, which is a major reason why it is a leading cause of cancer death. Signs and symptoms may not appear until pancreatic cancer is quite advanced and complete surgical removal isn't possible. Chemotherapy alone or in combination with surgery and/or radiation is does not alter long term prognosis.

It is therefore an object of the present invention to provide a new class of compounds for treatment of pancreatic cancer and other glutamine addicted cancers.

It is another object of the present invention to provide new compositions for treatment of pancreatic cancer and other glutamine addicted cancers.

It is a further object of the present invention to provide new delivery formulations demonstrating efficacy in treatment of pancreatic cancer using compounds not effective when administered by standard techniques.

SUMMARY OF THE INVENTION

Pancreatic ductal adenocarcinoma (PDAC) remains one of the most lethal diseases despite continual improvements in therapy. Thus new approaches are sorely needed. Mutations in the oncogenic KRAS gene occur in over 90% of PDACs with K-Ras being a known regulator of glutamine metabolism that renders cancer cells addicted to glutamine. Therefore, compounds and new compositions targeting glutamine metabolism should be particularly effective in treating pancreatic cancer, and would cover a substantial portion of PDAC.

The first step of glutamine metabolism is the conversion of glutamine to glutamate and ammonia via glutaminase (GLS). Small molecule glutaminase inhibitors, such as BPTES (bis-2-[5-(phenylacetamido)-1,3,4-thiadiazol-2-yl] ethyl sulfide) and its analogs, block the production of glutamine in pancreatic cancer cells (see FIG. 1) and cause delayed growth rates of glutamine-addicted pancreatic cancer in both in vitro and in vivo preclinical models.

Currently available glutaminase inhibitors are generally poorly soluble, metabolically unstable, and/or require high doses, which together reduce their efficacy and therapeutic index. These can be formulated into nanoparticles and delivered safely and effectively for treatment of pancreatic cancer and other glutamine addicted cancers. Studies demonstrate that nanoparticle delivery of BPTES, relative to use of BPTES alone, can be safely administered and provides dramatically improved tumor drug exposure, resulting in greater efficacy. GLS inhibitors can be administered in higher concentrations with sub-100 nm nanoparticles, since the nanoparticles package the drug into "soluble" colloidal nanoparticles, and the nanoparticles deliver higher drug exposure selectively to the tumors due to the enhanced permeability and retention (EPR) effect. These factors result in sustained drug levels above the IC50 within the tumors for days, providing significantly enhanced efficacy compared to unencapsulated drug.

Structural information about the binding of BPTES to glutaminase was used to develop inhibitors with substantially improved potency after a screen of 350,000 compounds failed to identify new inhibitors. These are primarily based on modifications to BPTES. Studies demonstrate efficacy and higher therapeutic indices relative to BPTES. The GLS inhibitors with enhanced potency, as well as nanoencapsulated GLS inhibitors, should provide an enhanced therapeutic index that can be safely administered at higher doses compared to free drug, thereby potentially resulting in greatly improved efficacy. The technology has widespread application for all glutamine addicted cancers, not just pancreatic cancer.

BRIEF DESCRIPTION OF THE DRAWINGS

FIGS. 3A-3D are graphs of KRAS mutated human pancreatic cancer cells showing sensitivity to glutamine deprivation. Human pancreatic cancer cells were grown at 37° C. in a 5% (v/v) $CO_2$ and 95% (v/v) air incubator in full DMEM media with and without glutamine. 90% of the KRAS mutation-pancreatic cancer cells derived from patients were sensitive to glutamine deprivation.

FIGS. 5A-5B are the Crystal structure of GLS in complex with BPTES (3VP1). (FIG. 5A shows GLS forming a tetramer with two molecules of BPTES (green), each of which binds to the dimer interface region. FIG. 5B is a magnified view of the BPTES binding site. The terminal phenylacetyl groups provide no specific interaction with the binding site. Glu325 is found in the vicinity of the phenylacetyl group and can be exploited to gain additional affinity.

FIG. 6 is a schematic of the proposed binding mode of compound 5 (cyan) to the BPTES binding site of GLS (3VOZ).

DETAILED DESCRIPTION OF THE INVENTION

I. Definitions

Figure 1:
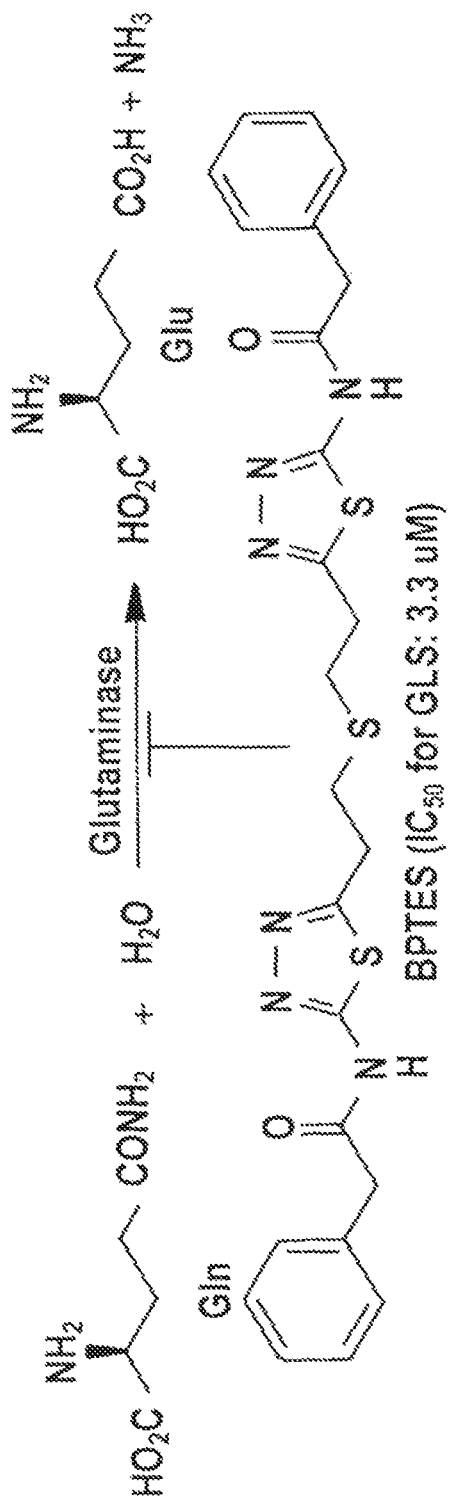
FIG. 1 is a schematic of the reaction catalyzed by GLS and the structure of allosteric GLS inhibitor BPTES.

As used herein, the term "aliphatic" refers to carbon moieties which may be acyclic or cyclic, completely saturated, partially saturated, and, for cyclic moieties, also includes aromatic systems.

The terms "biocompatible" as used herein refers to one or more materials that are neither themselves toxic to the host (e.g., an animal or human), nor degrade (if the polymer degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the polymer into smaller, non-polymeric subunits.

The term "corresponding particle" or "reference particles" as used herein refers to a particle that is substantially identical to another particle to which it is compared, but typically lacking a surface modification to promote transport differences through the pores in the ECM of the pancreas. A corresponding particle is typically of similar material, density, and size as the particle to which it is compared. In certain embodiments, a corresponding particle is a particle that does not have a dense coating of polyethylene glycol. In certain embodiments, a comparable particle is a particle that is not formed of a blended mixture containing free polymer and polymer conjugated to polyethylene glycol.

The term "densely coated particle" refers to a particle that is modified to specifically enhance the density of coating agent at the surface of the particle, for example, relative to a reference particle. In some embodiments, a densely coated particle is formed from a ratio of polyethylene glycol to polymer that is sufficient to alter the physicochemical properties of the particle relative to a less densely coated, or non-coated particle. In some embodiments, the density of coating agent is sufficient to completely mask the charge of the particle, resulting in a near neutral charge and near neutral zeta potential value and colloidal stability in physiological solutions. In a particular embodiment, a densely coated particle is achieved using branched polyethylene glycol or branched polymer, wherein the branching enhances the ratio of polyethylene glycol to polymer as compared to a reference particle that does not contain a branched polymer or branched polyethylene glycol.

The term "diameter" is art-recognized and is used herein to refer to either of the physical diameter or the hydrodynamic diameter. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles.

"Sustained release" as used herein refers to release of a substance over an extended period of time in contrast to a bolus type administration in which the entire amount of the substance is made biologically available at one time.

The term "microspheres", "microparticles", and "microcapsules are used interchangeably unless otherwise stated. These have a size between about one up to about 1000 microns. In general, "microcapsules," have a core of a different material than the shell material. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 100 nm, or less than 100 nm, such as 50 nm, or 10 nm.

A composition comprising microparticles or nanoparticles may include particles of a range of particle sizes. In certain embodiments, the particle size distribution may be uniform, e.g., within less than about a 20% standard deviation of the median volume diameter, and in other embodiments, still more uniform, e.g., within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "surfactant" refers to an agent that lowers the surface tension of a liquid.

The term "therapeutic agent" refers to an agent that can be administered to prevent or treat a disease or disorder.

Examples include, but are not limited to, a drug, a drug analog, a small molecule, a peptidomimetic, a protein, peptide, carbohydrate or sugar, lipid, or surfactant, or a combination thereof.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refer to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including chemically or physically couple, in physical admixture, or enveloping the agent in a coating layer

II. Compositions

Synthetic drug delivery platforms with a dense surface coating of hydrophilic and neutrally charged polymer such as polyethylene glycol (PEG) or polyethylene glycol-polyoxyethylene block copolymer known as poloxamer such as a PLURONIC® (referred to collectively as "PEGylated nanoparticles") which are capable of rapid diffusion and widespread distribution in pancreas or other glutamine addictive tissue are disclosed for delivery of safer, more efficacious dosages of glutaminase inhibitors to pancreatic tumors and other glutamine addicted tumors.

A. Nanoparticles

Nanoparticles are typically formed using a polymer such as the FDA approved polyhydroxy acids poly(lactic acid), poly(glycolic acid) or copolymer thereof, having a coating of a hydrophilic polymer such as polyethylene glycol (PEG) with enhances diffusion through tissues.

1. Core Polymer

Any number of biocompatible polymers can be used to prepare the nanoparticles. In preferred embodiments, the biocompatible polymer(s) is biodegradable. The polymer can be a branched polymer, to enhance the capacity of the polymer to conjugate to a coating agent such as PEG. Exemplary polymers include, but are not limited to, polymers prepared from lactones, such as poly(caprolactone) (PCL), polyhydroxy acids and copolymers thereof such as poly(lactic acid) (PL A), poly(L-lactic acid) (PLLA), poly (gly colic acid) (PGA), poly(lactic acid-co-glycolic acid) (PLGA), poly(L-lactic acid-co-glycolic acid) (PLLGA), poly(D,L-lactide) (PDLA), poly(D,L-lactide-co-caprolactone), poly(D-lactide-co-caprolactone-co-glycolide), poly (D,L-lactide-co-PEO-co-D,L~lactide), poly(D,L-lactide-co-PPO-co~D,L-lactide), and blends thereof, polyamino acids such as poly-L-lysine (PLL), poly(valeric acid), and poly-L-glutamic acid, polyanhydrides, polyesters, polyorthoesters, poly(ester amides), polyamides, polyalkylenes such as polyethylene and polypropylene, polyalkylene glycols such as poly(ethylene glycol) (PEG), polyalkylene oxides (PEO), polyvinyl alcohols (PVA), and polyhydroxyalkanoates, Copolymers of the above, such as random, block, or graft copolymers, or blends of the polymers listed above can also be used.

Functional groups on the polymer can be capped to alter the properties of the polymer and/or modify (e.g., decrease or increase) the reactivity of the functional group. For example, the carboxyl termini of carboxylic acid contain polymers, such as lactide- and glycolide-containing polymers, may optionally be capped, e.g., by esterification, and the hydroxyl termini may optionally be capped, e.g. by etherification or esterification.

In polymer chemistry, branching occurs by the replacement of a substituent, e.g., a hydrogen atom, on a monomer subunit, by another covalently bonded chain of that polymer; or, in the case of a graft copolymer, by a chain of another type. Branching may result from the formation of carbon-carbon or various other types of covalent bonds. Branching by ester and amide bonds is typically by a condensation reaction, producing one molecule of water (or HCl) for each bond formed.

The branching index measures the effect of long-chain branches on the size of a macromolecule in solution. It is defined as $g=<sb2>/<sl2>$, where sb is the mean square radius of gyration of the branched macromolecule in a given solvent, and sl is the mean square radius of gyration of an otherwise identical linear macromolecule in the same solvent at the same temperature. A value greater than 1 indicates an increased radius of gyration due to branching.

Examples of preferred natural polymers include proteins such as albumin, collagen, gelatin and prolamines, for example, zein, and polysaccharides such as alginate.

2. Coating Agents

Nanoparticles, coated with one or more materials that promote diffusion of the particles through the ECM in the pancreas by reducing interactions between the particles and pancreas tissue (e.g., surface altering agents) are disclosed. Examples of the surface-altering agents include, but are not limited to, polyethylene glycol ("PEG") and poloxomers (polyethylene oxide block copolymers).

A preferred coating agent is poly(ethylene glycol), also known as PEG. PEG may be employed to reduce adhesion in pancreas ECM in certain configurations, e.g., wherein the length of PEG chains extending from the surface is controlled (such that long, unbranched chains that interpenetrate into the ECM are reduced or eliminated). For example, linear high MW PEG may be employed in the preparation of particles such that only portions of the linear strands extend from the surface of the particles (e.g., portions equivalent in length to lower MW PEG molecules). Alternatively, branched high MW PEG may be employed. In such embodiments, although the molecular weight of a PEG molecule may be high, the linear length of any individual strand of the molecule that extends from the surface of a particle would correspond to a linear chain of a lower MW PEG molecule.

Representative PEG molecular weights in daltons (Da) include 300 Da, 600 Da, 1 kDa, 2 kDa, 3 kDa, 4 kDa, 5 kDa, 6 kDa, 8 kDa, 10 kDa, 15 kDa, 20 kDa, 30 kDa, 50 kDa, 100 kDa, 200 kDa, 500 kDa, and 1 MDa. In preferred embodiments, the PEG has a molecular weight of about 5,000 Daltons. PEG of any given molecular weight may vary in other characteristics such as length, density, and branching. In a particular embodiment, a coating agent is methoxy-PEG-amine, with a MW of 5 kDa. In another embodiment, a coating agent is methoxy-PEG-N-hydroxysuccinimide with a MW of 5 kDa (mPEG-NHS 5 kDa).

In alternative embodiments, the coating is a poloxamer such as the polyethylene glycol-polyethylene oxide block copolymers marketed as PLUORONICs®.

The core polymer or PEG can be a branched polymer that is capable of enhancing conjugation of the coating agent and core polymer. Exemplary branched polymers include 25 kDa branched polyethyleneimine (PEI) and 5 kDa branched methoxy-PEG.

iii. Copolymers

In preferred embodiments, copolymers of PEG or derivatives thereof with any of the polymers described above may be used to make the polymeric particles. In certain embodiments, the nanoparticles are formed under conditions that allow regions of PEG to phase separate or otherwise locate to the surface of the particles, with they hydrophobic polymer forming the core. The surface-localized PEG regions alone may perform the function of, or include, a surface-altering agent.

iv. Density of Coating Agent

In preferred embodiments the nanoparticles are coated with PEG or other coating agent at a density that optimizes rapid diffusion through the pancreas parenchyma. The density of the coating can be varied based on a variety of factors including the material and the composition of the particle.

In a preferred embodiment the co-polymer molar ratio of PEG or other coating agent to polymer is greater than 8 (i.e., more than 8 moles of PEG to every mole of polymer). The ratio by moles of PEG or other coating agent to polymer can be 9, 10, 11, 12, 13, 14 15, 16, 17, 18, 19, 20, 21, 22, 23, 24, 25, 26, 27, 28, 29, 30, 37, 50 or more than 50. A preferred molar ratio of PEG or other coating agent to polymer is 26. In one embodiment, the density of the PEG or other coating agent is at least 0.001, 0.002, 0.005, 0.01, 0.02, 0.05, 0.1, 0.2, 0.5, 1, 2, 5, 10, 20, 50, or 100 units per $nm^2$.

In another embodiment, the amount of the PEG or other coating agent is expressed as a percentage of the mass of the particle. In a particular embodiment, the mass of the PEG or other coating agent is at least 1/10,000, 1/7500, 1/5000, 1/4000, 1/3400, 1/2500, 1/2000, 1/1500, 1/1000, 1/500, 1/250, 1/200, 1/150, 1/100, 1/75, 1/50, 1/25, 1/20, 1/5, 1/2, or 9/10 of the mass of the particle. In a further embodiment, the weight percent of the PEG or other coating agent is at least 80%, 81%, 82%, 83%, 84%, 85%, 86%, 87%, 88%, 89%, 90%, 91%, 92%, 93%, 94%, 95%, or greater.

Surface density of poly(ethylene glycol) (PEG) on nanoparticles is a key parameter in determining their successful applications in vivo. The dense coating of PEG on biodegradable nanoparticles can allow rapid penetration through tissue because of the greatly reduced adhesive interaction.

Different methods have been employed to assess the surface PEG density on nanoparticles, including those that directly measure changes to physiochemical properties of nanoparticles, such as surface charge and hydrodynamic diameter. The reactions of dye and reagents (such as fluorescence dye) to functional PEG were widely used for PEG quantification. Nuclear magnetic resonance (NMR) can be used to assess the surface. Quantitative 1H nuclear magnetic resonance (NMR) can be used to measure the surface PEG density on nanoparticles. The density of the coating can be varied based on a variety of factors including the surface altering material and the composition of the particle. In one embodiment, the density of the surface altering material, such as PEG, as measured by 1H NMR is at least, 0.1, 0.2, 0.5, 0.8, 1, 2, 5, 8, 10, 15, 20, 25, 40, 50, 60, 75, 80, 90, or 100 chains per nm. The range above is inclusive of all values from 0.1 to 100 units per $nm^2$.

B. Glutaminase Inhibitors

Glutaminase inhibitors are known and available. As described in the examples, these may be modified to improve pharmacokinetics and efficacy, as well as encapsulated as described above to avoid degradation and metabolism during delivery.

In certain embodiments, the glutaminase inhibitor may be selected from a compound of Formula (1)

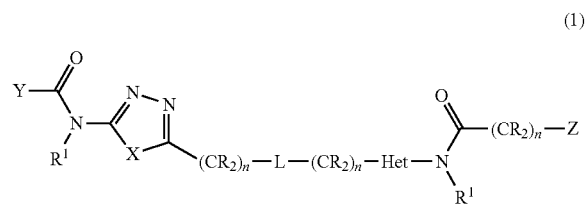

(1)

wherein $R^1$ is independently selected from hydrogen, $C(=O)C_{1-10}$ aliphatic, $C(=O)OC_{1-10}$ aliphatic and $C_{1-10}$ aliphatic;

Het is either absent or a substituted or unsubstituted heterocycle

L is absent, or selected from —CH=CH—, —C≡C—, O, S, $SO_2$ or $NR^1$;

X represents —CH=CH—, O, S, $SO_2$ or $NR^1$;

n is independently selected from 0-10;

R is in each case independently selected from hydrogen, $C_{1-10}$ aliphatic, alkoxy or hydroxy, or the two R groups on the same carbon atom may form an oxo, and wherein two or more R groups on the same or different carbon atoms may form a ring;

Y and Z independently represent substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R^8)(R^9)(R^{10})$, $N(R^4)(R^5)$ or $OR^5$, wherein any free hydroxyl group may be acylated to form $C(=O)R^7$;

$R^4$ and $R^5$ each independently for each occurrence represent hydrogen or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(=O)R^7$;

R[7] represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, R[8], R[9] and R[10] each independently for each occurrence represent hydrogen or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or R[8] and R[9] together with the carbon to which they are attached, form a carbocyclic or heterocyclic ring system, wherein any free hydroxyl group may be acylated to form C(=O)R[7], and wherein at least two of R[8], R[9] and R[10] are not hydrogen;

R[11] represents aryl, arylalkyl, aryloxy, aryloxyalkyl, heteroaryl, heteroarylalkyl, heteroaryloxy, or heteroaryloxyalkyl, wherein the aryl or heteroaryl ring is substituted with either —OCHF$_2$ or —OCF$_3$ and is optionally further substituted, or R[11] represents C(R[12])(R[13])(R[14]), N(R[4])(R[14]) or OR[14], wherein any free hydroxyl group may be acylated to form C(=O)R[7];

R[12] and R[13] each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(=O)R[7], and wherein both of R[12] and R[13] are not hydrogen; and R[14] represents aryl, arylalkyl, aryloxy, aryloxyalkyl, heteroaryl, heteroarylalkyl, heteroaryloxy, or heteroaryloxyalkyl, wherein the aryl or heteroaryl ring is substituted with either —OCHF$_2$ or —OCF$_3$ and is optionally further substituted.

In other embodiments, the glutaminase inhibitor may be a compound of Formula (2):

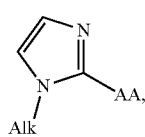

(2)

wherein AA represents an optionally protected amino acid group and Alk represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or C(R[8])(R[9])(R[10]), N(R[4])(R[5]) or OR[5], wherein any free hydroxyl group may be acylated to form C(=O)R[7] wherein R[4]-R[10] have the above meanings given above.

In other embodiments, the glutaminase inhibitor may be selected from a compound of Formula (3):

(3)

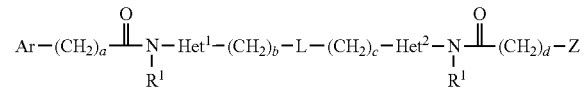

wherein
Ar is an optionally substituted aryl ring;
R[1], L, and Z have the meaning given above, and
Het[1] is an optionally substituted heterocyclic ring;
a and d are independently selected from 0-10;
b and c are independently selected from 0-5;
Het[2] is absent, or is an optionally substituted heterocyclic ring.

For the compound of Formula (3), it is preferred that Ar is an aryl ring selected from:

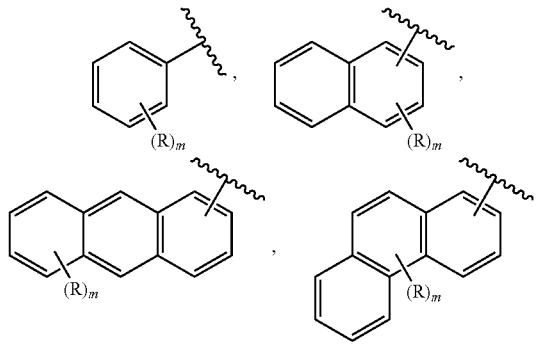

wherein

indicates that the ring system may be attached at any atom in the ring,
m is selected from 0-3; and
R is independently selected from a $C_{1-10}$ aliphatic group, a halogen, a hydroxyl, a trifluoromethyl group, an O—$C_{1-10}$ aliphatic group, a C(=O)O—$C_{1-10}$ aliphatic group, an OC(=O)—$C_{1-10}$ aliphatic group, a cyano, a nitro, NH$_2$, NH(ali), N(ali)$_2$, wherein (ali) represents a $C_{1-10}$ aliphatic group, and wherein in the case of N(ali)$_2$ the two aliphatic groups may form a ring, an azido, a thiol, an S—$C_{1-10}$ aliphatic group, a $C_{1-10}$ aliphatic-O—$C_{1-10}$ aliphatic group, a $C_{1-10}$ aliphatic-C(=O)O—$C_{1-10}$ aliphatic group, a $C_{1-10}$ aliphatic-OC(=O)—$C_{1-10}$ aliphatic group, and a heterocyclic group.

In other embodiments, the glutaminase inhibitor is selected from a compound of Formula (4)

(4)

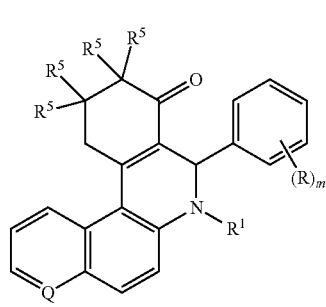

wherein m, R, R[1] and R[5] have the meanings given above, and Q is either CH or N.

In some embodiments, the heterocycles present in the compounds disclosed herein are selected from optionally substituted benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, 1,2,3 triazole, 1,2,4 triazole and xanthenyl.

Especially preferred heterocycles include 1,2,4 thiadiazolyl, pyridazinyl, morpholinyl, pyrrolidinyl, imidazolyl, benzimidazolyl, tetrazolyl, 1,2,3 triazole, 1,2,4 triazole, isoxazolyl, isothiazolyl, wherein each heterocycle may be substituted one or more times by OH, COOH, NH$_2$ or SH.

Two independent groups published crystal structures of GLS in complex with BPTES, revealing the unique allosteric binding of BPTES to the dimer interface of GLS tetramer. These findings provided a structural basis for BPTES' unique ability to selectively inhibit GLS over other glutamine utilizing enzymes including GLS2. The structural information underscores the pharmacological advantage (selectivity to GLS) of BPTES and its analogs and enables more rational approach for optimizing potency and led to analogs which exhibit >30-fold improvement in potency compared to BPTES (IC50=100 nM vs 3 μM), as demonstrated in the examples.

In another embodiment, the glutaminase inhibitor is a compound of Formula (1):

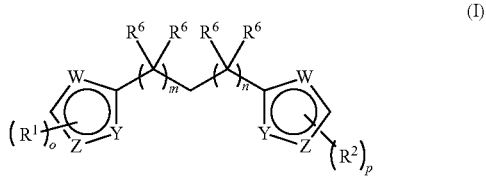

(I)

such as disclosed in U.S. Published Patent Application 2014/0142146, to Lemieux et al., and wherein each variable is defined by Lemieux at paragraphs [0004-0023].

In other embodiments, the glutaminase inhibitor is acivicin, 6-diazo-5-oxo-L-norleucine, azaserine, ebselen, chelerythrine or apomorphine. Experiments in the 1950s showed that the compounds 6-diazo-5-oxo-L-norleucine (L-DON) and azaserine, isolated from a species of *Streptomyces*, have significant activity as glutamine analogues. Later, another glutamine analogue, acivicin, was also isolated. Research on the glutamine dependency of cell lines in vitro spurred the testing of these compounds as therapeutics. Preclinical testing of all three agents showed a significant cytotoxic effect against certain tumor types both in culture and in mouse xenograft models. Although all three of these agents showed clinical activity, their use was discontinued due to dose-limiting neurotoxicity, gastrointestinal toxicity, and myelosuppression. All three compounds show their greatest activity in inhibiting the glutamine-dependent enzymatic steps in nucleotide biosynthesis. In fact, acivicin has only a minor effect on glutaminolysis, while significantly reducing glutamine-dependent nucleotide biosynthesis. These studies demonstrate that glutamine mimetics are unduly toxic. This toxicity is believed to be reduced when the compounds are encapsulated in nanoparticles for delivery to the target cells.

Because these agents non-selectively target glutamine-consuming processes, compounds directed at specific nodes of glutamine metabolism have also been tested. ASCT2, the Na$^+$-dependent neutral amino acid transporter encoded by SLC1A5, is broadly expressed in lung cancer cell lines and accounts for a majority of glutamine transport in those cells. It has been shown that γ-L-glutamyl-p-nitroanilide (GPNA) inhibits this transporter and limits lung cancer cell growth. Additional interest in GPNA lies in its ability to enhance the uptake of drugs imported via the monocarboxylate transporter MCT1. Suppressing glutamine uptake with GPNA enhances MCT1 stability and stimulates uptake of the glycolytic inhibitor 3-bromopyruvate (3-BrPyr). Because enforced MCT1 overexpression is sufficient to sensitize tumor xenografts to 3-BrPyr, GPNA may be useful in 3-BrPyr-based therapeutic regimens.

C. Pharmaceutical Excipients for Delivery to the Pancreas or Other Tumors

The particles may be administered in combination with a physiologically or pharmaceutically acceptable carrier, excipient, or stabilizer. Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In preferred embodiments, the particles are formulated for parenteral delivery to the pancreas. Typically the particles will be formulated in sterile saline or buffered solution for injection into the tissues or cells to be treated. The particles can be stored lyophilized in single use vials for rehydration immediately before use. Other means for rehydration and administration are known to those skilled in the art.

Optional pharmaceutically acceptable excipients include, but are not limited to, lubricants, disintegrants, colorants, stabilizers, and surfactants. Stabilizers are used to inhibit or retard decomposition reactions which include, by way of example, oxidative reactions.

The nanoparticles or nanoconjugates can be formulated in dosage unit form for ease of administration and uniformity of dosage. The expression "dosage unit form" as used herein refers to a physically discrete unit of conjugate appropriate for the patient to be treated. It will be understood, however, that the total daily usage of the compositions will be decided by the attending physician within the scope of sound medical judgment. For any nanoparticle or nanoconjugate, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans.

Therapeutic efficacy and toxicity of conjugates can be determined by standard pharmaceutical procedures in cell cultures or experimental animals, e.g., ED50 or IC50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies can be used in formulating a range of dosages for human use.

D. Combinations with Additional Chemotherapeutics and Radiation

Figure 2:
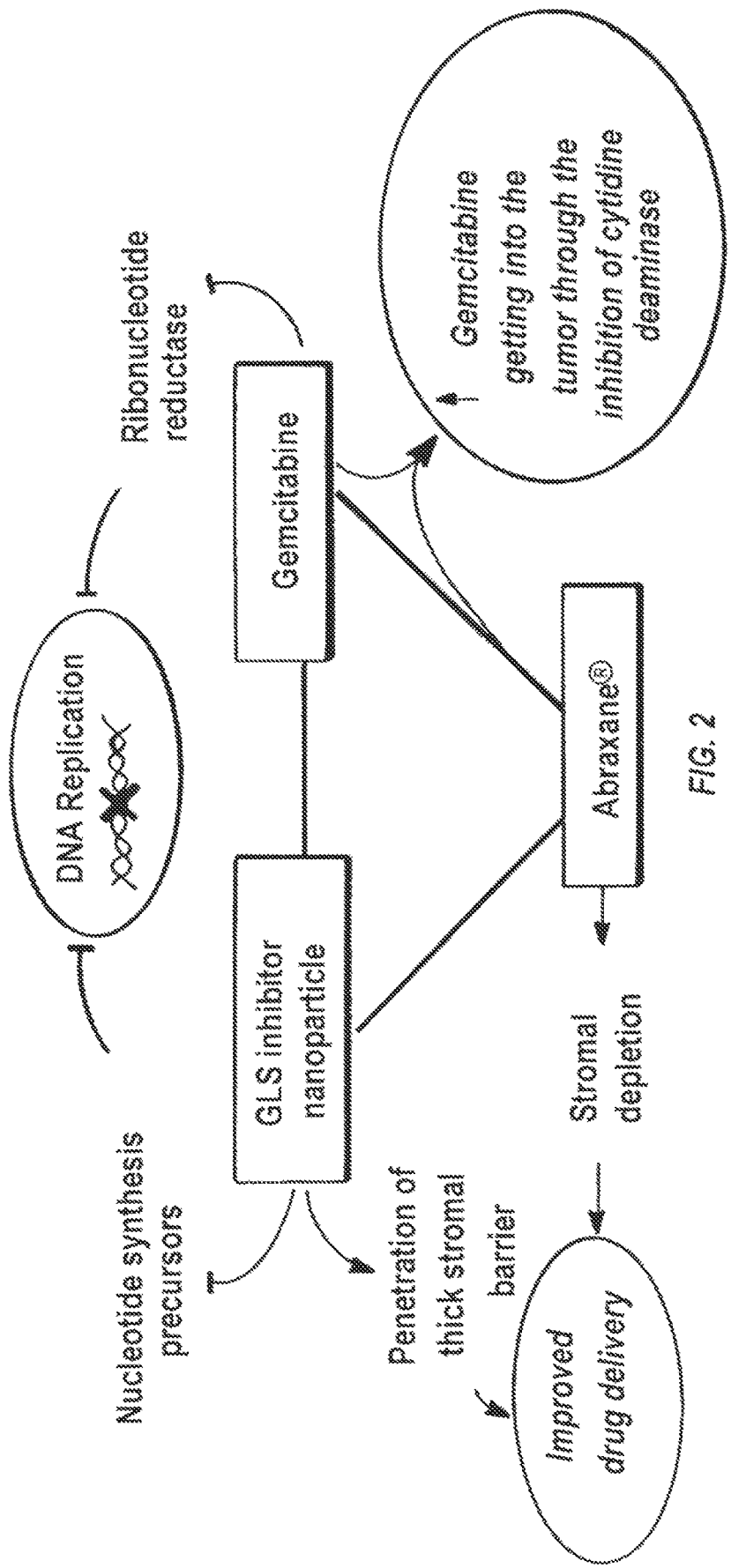
FIG. 2 is a schematic of the strategy of blocking GLS in combination with other chemotherapeutics.

It is expected that combining the nanoparticulate glutaminase inhibitors with other chemotherapeutics, such as gemcitabine and the modified taxol ABRAXANE®, will enhance targeting multiple metabolic pathways in pancreatic cancer that will lead to significantly improved therapy. See FIG. 2.

Accepted protocols such as administration of Gemcitabine and capecitabine or erlotinib, with or without 5-FU/capecitabine-based chemoradiation, administration of a Platinum analog such as cisplatin or oxaliplatin or fluoropyrimidine can be enhanced by co-administration with the nanoparticulate glutaminase inhibitor.

Other therapeutic, prophylactic and/or diagnostic agents can be co-delivered depending on the application. These additional active agents can be administered separately, systemically or locally, by injection, infusion, or orally, and/or dispersed in the nanoparticles or be covalently attached to one or more of the polymeric components of the nanoparticle.

Suitable additional active agents include, but are not limited to, other drug-based medicine, anti-inflammatory drugs, antiproliferatives, chemotherapeutics, vasodilators, and anti-infective agents. In certain embodiments, the nanoparticles contain one or more antibiotics, such as tobramycin, colistin, or aztreonam. The disclosed nanoparticles can optionally contain one or more antibiotics which are known to possess anti-inflammatory activity, such as erythromycin, azithromycin, or clarithromycin. Nanoparticles may also be used for the delivery of chemotherapeutic agents or anti-proliferative agents.

II. Methods of Manufacture

A. Polymer Preparation

The polymers can be synthesized by any means known in the art. PEG or other coating agents can be conjugated to the core polymer using a variety of techniques known in the art depending on whether the coating is covalently or non-covalently associated with the particles.

In some embodiments the PEG or other coating agent can be covalently attached to the core polymer by reacting functional groups on the particles with reactive functional groups on the PEG or other coating agent to make a copolymer. For example, aminated PEG can be reacted with reactive functional groups on the particles, such as carboxylic acid groups, to covalently attach the agent via an amide bond.

In some embodiments nanoparticles are formed of a mixture of PEGylated and non-PEGylated polymers. The non-PEGylated polymers can contribute a defined amount of the total free amines, such as 5%, 10%, 15%, 20%, 25%, 30%, 35%, 40%, 45%, 50% or more than 50% of the total free amines in the particles.

B. Nanoparticles

The disclosed nanoparticles can be formed from one or more core polymers and one or more PEGs or other coating agents. The methods employed for nanoparticle formation will depend on a variety of factors, including the characteristics of the polymers present in the nanoparticle, as well as the desired particle size and size distribution.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing nanoparticles include, but are not limited to, solvent evaporation, solvent removal, spray drying, phase inversion, low temperature casting, and nanoprecipitation. Suitable methods of particle formulation are briefly described below. The preferred method is emulsion. Pharmaceutically acceptable excipients, including pH modifying agents, disintegrants, preservatives, and antioxidants, can optionally be incorporated into the particles during particle formation. As described above, one or more additional active agents can also be incorporated into the nanoparticle during particle formation.

1. Solvent Evaporation

In this method the polymer is dissolved in a volatile organic solvent, such as methylene chloride. Drug is added to the solution, and the mixture is suspended in an aqueous solution that contains a surface active agent such as PEG. The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

2. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

3. Spray-Drying

In this method, the polymer is dissolved in solvent. A known amount of the active drug is suspended (insoluble drugs) or co-dissolved (soluble drugs) in the polymer solution. The solution or the dispersion is then spray-dried.

4. Phase Inversion

Particle can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or drugs. In the process, the polymer is dissolved in an organic solvent and then contacted with a non-solvent, which causes phase inversion of the dissolved polymer to form small spherical particles, with a narrow size distribution optionally incorporating an antigen or other substance.

Other methods known in the art that can be used to prepare nanoparticles include, but are not limited to, polyelectrolyte condensation (see Suk et al., *Biomaterials*, 27, 5143-5150 (2006)); single and double emulsion (probe sonication); nanoparticle molding, and electrostatic self-assembly (e.g., polyethylene imine-DNA or liposomes).

IV. Methods of Use

A. Types of Cancers to be Treated

Glutamine is the most abundant amino acid in the bloodstream. Glutamine supplies nitrogen for nucleobase synthesis and carbon for the tricarboxylic acid cycle (TCA), lipid synthesis, and nucleotide synthesis. The catabolism of glutamine into glutamate, aspartate, $CO_2$, pyruvate, lactate, alanine and citrate is called glutaminolysis. The first step of glutaminolysis is the conversion of glutamine to glutamate and ammonia via GLS. Glutaminolysis is upregulated in many cancer cells. It has been found that human pancreatic cancer cells were dependent upon glutamine for survival despite being grown in glucose-rich medium. This state is known as "glutamine addiction". KRAS mutations have been found to explain glutamine-dependence in pancreatic cancer. Therefore, dependency on glutamine can be exploited to develop new cancer treatments.

Some cancers display addiction to glutamine despite the fact that glutamine is a nonessential amino acid that can be synthesized from glucose. The high rate of glutamine uptake exhibited by glutamine-dependent cells does not appear to result solely from its role as a nitrogen donor in nucleotide and amino acid biosynthesis. Instead, glutamine plays a required role in the uptake of essential amino acid and in maintaining activation of TOR kinase. Moreover, in many cancer cells, glutamine is the primary mitochondrial substrate and is required to maintain mitochondrial membrane potential and integrity as well as support of the NADPH production needed for redox control and macromolecular synthesis. The growing cancer must synthesize nitrogenous compounds in the form of nucleotides and NEAAs. Glutamine is the obligate nitrogen donor in as many as three independent enzymatic steps for purine synthesis (phosphoribosylpyrophosphate (PRPP) amidotranferase, phosphoribosylformylglycinamidine (FGAM) synthetase, GMP synthetase) and in two independent enzymatic steps for pyrimidine synthesis (carbamoyl phosphate synthetase II, CTP synthetase). In these reactions, glutamine donates its amide (γ nitrogen) group and is converted to glutamic acid in the process.

Studies using quantitative RT-PCR and chromatin-immunoprecipitation (ChIP) in multiple cell systems have suggested that c-MYC (Myc) binds and transactivates eleven genes involved in nucleotide biosynthesis. Myc is a basic helix-loop-helix zipper (bHLHZ) protein that heterodimerizes with the small bHLHZ protein MAX and exerts both activating and repressing transcriptional effects. Of the five enzymatic steps utilizing glutamine, three (PRPP amidotransferase, carbamoyl phosphate synthetase II, CTP synthetase) are directly regulated by Myc at the transcriptional level. Carbamoyl phosphate synthetase II, a rate-limiting glutamine-dependent enzyme involved in pyrimidine synthesis, has also been found to be regulated via epidermal growth factor receptor (EGFR)-dependent mitogen-activated protein kinas (MAPK) phosphorylation as well as caspase-dependent degradation.

Cancer cells take up and metabolize glucose and glutamine to a degree that far exceeds their needs for these molecules in anabolic macromolecular synthesis. Quantitative RT-PCR and ChIP experiments support Myc's binding and transcriptional activation of two high affinity glutamine transporters: SLC38A5 (also called SN2) and SLC1A5 (ASCT2), the transporter required for glutamine-dependent mTORC1 activation. In addition to facilitating glutamine uptake, Myc promotes the metabolism of imported glutamine into glutamic acid and ultimately into lactic acid. Myc-induced metabolic reprogramming triggers cellular dependency on exogenous glutamine as a source of carbon for the maintenance of the mitochondrial membrane potential and macromolecular synthesis. The cell death induced by glutamine starvation can be rescued by the overexpression of Bcl-2, Bcl-$x_L$, or a dominant negative form of caspase-9, implicating the intrinsic apoptotic pathway as the mechanism of cell death.

A wide variety of human cancer cell lines have shown sensitivity to glutamine starvation, including those derived from pancreatic cancer, glioblastoma multiforme, acute myelogenous leukemia, and small cell lung cancer. Although described herein with specific reference to pancreatic cancer, it will be understand that the compositions, methods of manufacture and administration to treat pancreatic cancer will be applicable to the treatment of other types of cancers.

Pancreatic ductal adenocarcinoma (PDAC) remains one of the most lethal diseases despite continual improvements in therapies. The inherited and acquired mutations believed to cause pancreatic cancer, such as KRAS, AKT, MYC, PI3K, and TP53, are known to re-program cancer metabolism to enable cells to survive and proliferate in the hypoxic and nutrient-deprived tumor microenvironment. KRAS mutations occur in over 90% of PDAC, and KRAS is a known regulator of glutamine metabolism. Therefore, targeting glutamine metabolism should be particularly effective in treating pancreatic cancer.

B. Methods of Administration and Dosing

The nanoparticles can be administered by a variety of routes of administration. In certain embodiments the particles are administered directly to the tumor. In other embodiments the particles are administered systemically.

Mechanisms for the enhanced delivery of the disclosed nanoparticles to the tumor are disclosed. Enhanced local delivery can be achieved via convection, electromagnetic, or other forces. Enhanced systemic delivery can be achieved via co- or sequential administration with permeabliization agents such as but not limited to pharmacologic substances (e.g. cytokines), mechanical barrier disruption (e.g. ultrasound), or osmotic changes (e.g. mannitol). Other methods of delivery include intrathecal or intra-ventricular delivery via cerebro-spinal fluid spaces, intra-nasal administration or delivery via the olfactory bulb and systemic delivery via oral, intravenous, or intra-arterial administration.

In general the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

Regardless of systemic, intrathecal, or local delivery into the tumor parenchyma itself, penetration of bioactive or imaging agents in the tumor and other tissues has been a key hurdle to effective therapy and diagnostics. Numerous studies using viral, nanoparticle, and convection-enhanced delivery have failed due to limited movement of substances within the tumor. Therefore, defining the critical limiting parameters and designing strategies to enhance tumor penetration will likely improve the efficacy of these treatments. Densely-pegylated nanoparticles offer numerous additional advantages, including increased particle diffusion, improved stability, and prolonged sustained-release kinetics. These factors are known to correlate with the efficacy of many therapeutics and will likely have a significant impact on the utility of nano-sized carriers for diagnostic and therapeutic delivery to the tumor.

The present invention will be further understood by the following non-limiting examples.

Example 1: Testing of Glutamine Deprivation on Pancreatic Cancer Cells

Materials and Methods

Dr. Le at the Division of Gastrointestinal and Liver Pathology, John Hopkins University, has a large collection of pancreatic cancer cell lines and xenografted pancreatic tumor specimens resected from patient samples at the time of surgery. These patients had not undergone chemotherapy or radiation therapy before surgery. Grafted tumors are subsequently transplanted from mouse to mouse and maintained as a live PancXenoBank and have been shown to retain their in vivo growth characteristics.

KRAS mutations render over 90% of pancreatic cancer cells addicted to glutamine, thereby conferring sensitivity to glutamine deprivation and GLS inhibition. Both of the pancreatic cancer models used herein closely recapitulate the clinical, pathologic, genetic and molecular aspects of human PDACs: the patient-derived orthotopic xenograft model uses patient tumors with KRAS mutations, and the KrasLSL.G12D/+; p53R172H/+; PdxCretg/+ (or KPC) model develops natural pancreatic tumors with characteristic stroma be tested in both rigorous models of this devastating form of cancer.

Results

90% of the KRAS mutation-pancreatic cancer cells derived from patients were sensitive to glutamine deprivation (FIGS. 3A and 3B), indicating GLS inhibition could have an impact in a high fraction of patients.

Figure 4A:
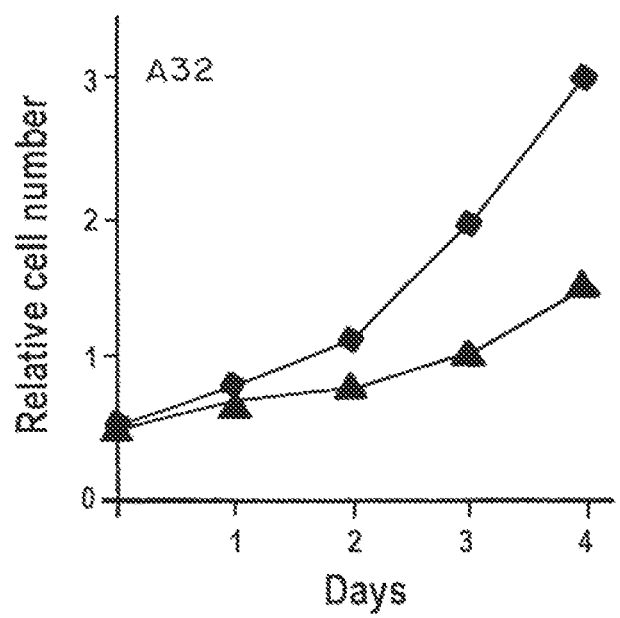
FIGS. 4A-4B are graphs showing the effect of PBTES on the growth of pancreatic cancer cell lines and xenografted pancreatic tumor specimens resected from patient samples at the time of surgery. These patients had not undergone chemotherapy or radiation therapy before surgery. Grafted tumors are subsequently transplanted from mouse to mouse and maintained as a live PancXenoBank which have been shown to retain their in vivo growth characteristics. To further examine the "glutamine addiction" phenotype in pancreatic cancer, the small molecule GLS inhibitor BPTES was administered to several of these glutamine-addicted pancreatic cancers and found to be inhibitory to their growth. Cells were grown at 37° C. in a 5% (v/v) $CO_2$ and 95% (v/v) air incubator in full DMEM media. BPTES was dissolved in DMSO. Relative cell number versus time in Days.
Figure 4B:
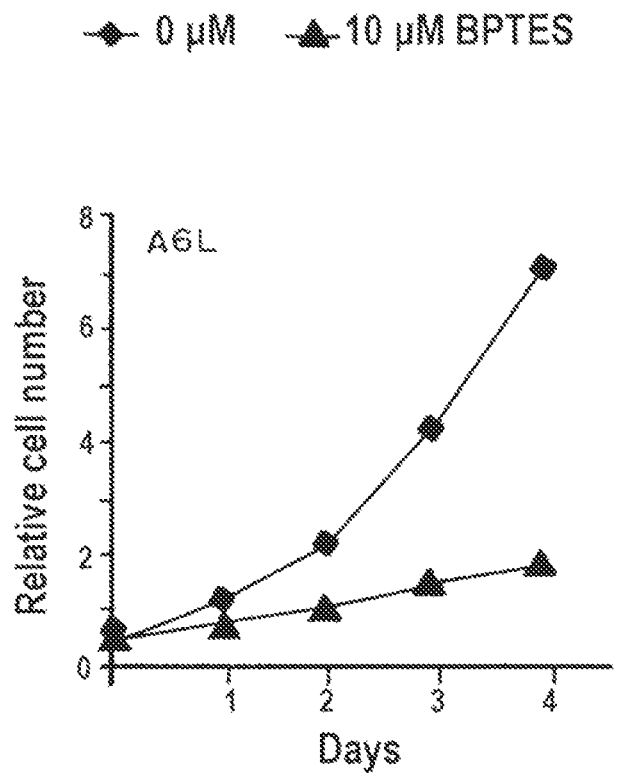

To examine the "glutamine addiction" phenotype in pancreatic cancer, the small molecule GLS inhibitor BPTES was tested on several of these glutamine-addicted pancreatic cancers and found that it was inhibitory to their growth (FIGS. 4A and 4B). KRAS-mutant human pancreatic cancer cells were exquisitely sensitive to both glutamine deprivation and the glutaminase (GLS) inhibitor BPTES.

Example 2: Screening for GLS Inhibitors; Design of New GLS Inhibitors

Materials and Methods

A high throughput screening (HTS) assay and together with NCATS screened over 350,000 compounds in attempt to identify novel GLS inhibitor structures. No tractable hit compounds were identified, which led to alternative approaches for circumventing the problem associated with BPTES, including taking advantage of its lipophilic nature by encapsulating the molecule into nanoparticles for sustained drug delivery. The significance of this approach is that the compounds share BPTES' antiproliferative effects without suffering from its poor solubility and metabolic stability.

The main objective was then to identify GLS inhibitors with improved potency while retaining a similar degree of lipophilicity with BPTES to ensure compatibility with nanoparticle formulation. Two distinct lines of medicinal chemistry efforts were used for design and synthesis of new GLS inhibitors.

Results a) Focused Structural Optimization Using Compound 3 as a Chemical Template.

Figure 13A:
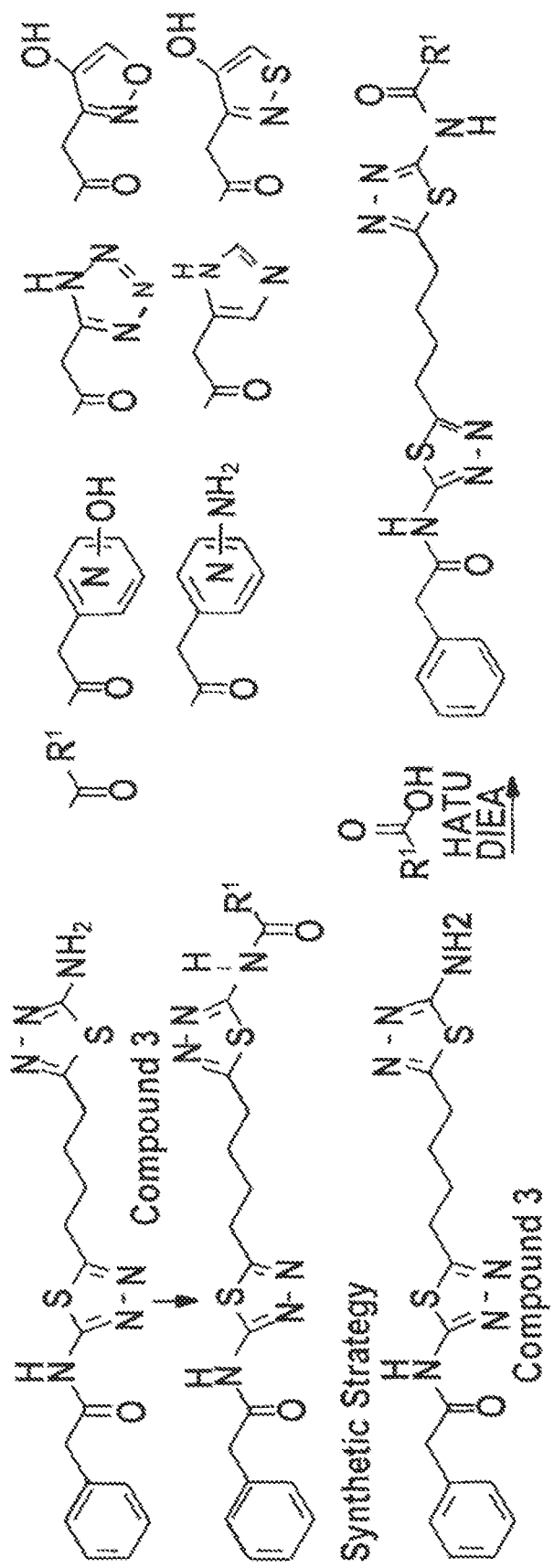
FIGS. 13A-13C are schematics to identify GLS inhibitors with improved potency while retaining a similar degree of lipophilicity with BPTES to ensure compatibility with nanoparticle formulation. Two distinct lines of medicinal chemistry efforts were used for design and synthesis of new GLS inhibitors. Conduct focused structural optimization using compound 3 as a chemical template. In the first set of SAR studies (Scheme 1, FIG. 13A), a variety of functional groups were incorporated into compound 3 in an attempt to form electrostatic interactions with Arg317/Glu325. The advantage of compound 3 over compound 1 is the lack of the metabolically liable sulfide moiety. Some of the acyl groups to be explored are illustrated in Scheme 1 (FIG. 13A). The common feature of these new target compounds is the existence of a hydrogen bond donor designed to interact with the Arg317. Some fragments contain a hydrogen bond acceptor (e.g., pyridine ring), which likely interact with the carboxylate group of Glu325, possibly forming a "triad" complex with GLS. Additionally, based on the preliminary biological screening of the compounds shown in Scheme 1, further modifications could involve substituting the new acyl moieties on both of the amines of the thiadiazole instead of just one thiadiazole. As shown in Scheme 1, all of these target compounds can be synthesized from compound 3 using conventional synthetic methodology employing HATU peptide coupling. In the second set of SAR studies (Scheme 2, FIG. 13B), compound 4 was used as a template and e the possibility of enhancing the interaction with Arg317/Glu325 by replacing the pyrrolidine group was studied. The nitrogen atom of the pyrrolidine ring in compound 4 serves as a hydrogen bond acceptor by interacting with Glu325. As shown in Scheme 2, the new target compounds contain a hydrogen bond donor to establish additional interaction with Arg317 to improve affinity to GLS. These analogs can be prepared from the carboxylic acid 8 undergoing HATU peptide coupling with 2-bromoethane-1-amine followed by alkylation with the secondary amine (NHR1R2) of choice. A scheme to expand the structural diversity by incorporating a pyridazine ring is shown in Scheme 3, FIG. 13C, which has previously been confirmed to serve as a replacement for the thiadiazole ring of BPTES-type GLS inhibitors.

In the first set of SAR studies (Scheme 1, FIG. 13A), a variety of functional groups were incorporated into compound 3 in an attempt to form electrostatic interactions with Arg317/Glu325. The advantage of compound 3 over compound 1 is the lack of the metabolically liable sulfide moiety. Some of the acyl groups to be explored are illustrated in Scheme 1. The common feature of these new target compounds is the existence of a hydrogen bond donor designed to interact with the Arg317. Some fragments contain a hydrogen bond acceptor (e.g., pyridine ring), which likely interact with the carboxylate group of Glu325, possibly forming a "triad" complex with GLS.

Additionally, based on the preliminary biological screening of the compounds shown in Scheme 1 (FIG. 13A) further modifications could involve substituting the new acyl moieties on both of the amines of the thiadiazole instead of just one thiadiazole. As shown in Scheme 1 (FIG. 13A), all of these target compounds can be synthesized from compound 3 using conventional synthetic methodology employing HATU peptide coupling.

b) Conduct Focused Structural Optimization Using Compound 4 as a Chemical Template.

Figure 13B:
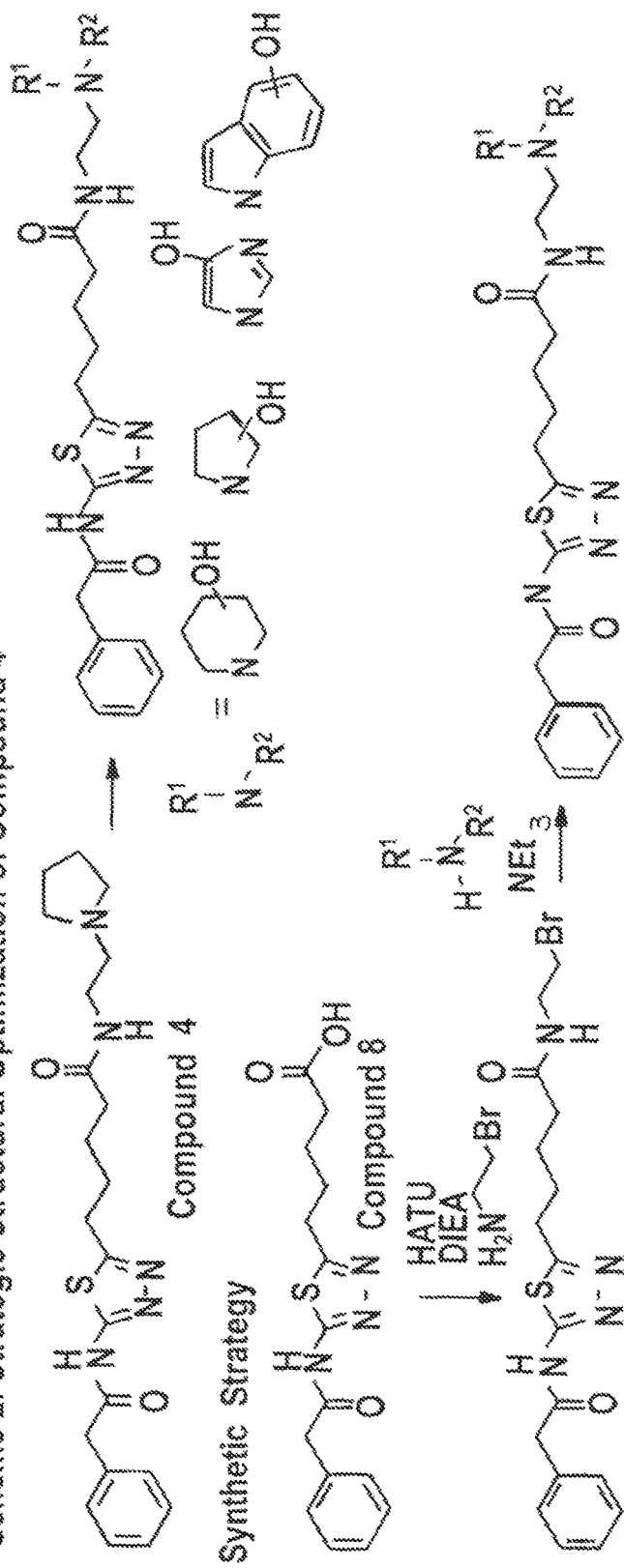

In the second set of SAR studies (Scheme 2, FIG. 13B), compound 4 was used as a template and the possibility of enhancing the interaction with Arg317/Glu325 explored by replacing the pyrrolidine group. The nitrogen atom of the pyrrolidine ring in compound 4 serves as a hydrogen bond acceptor by interacting with Glu325. As shown in Scheme 2, the new target compounds contain a hydrogen bond donor to establish additional interaction Arg317 to improve affinity to GLS. These analogs can be prepared from the carboxylic acid 8 undergoing HATU peptide coupling with 2-bromoethane-1-amine followed by alkylation with the secondary amine (NHR1R2) of choice.

The combination of the two distinct structural optimization approaches coupled with structure-based drug design will allow generation of rationally designed, structurally diverse compounds in a systematic manner.

All new synthetic compounds can be tested for their ability to inhibit GLS using an already established radioactive assay. Inhibitory-potency data will be continuously evaluated in relation to the chemical structure to further optimize structures for the most potent inhibitory activity with optimal lipophilicity. Potent (IC50≤200 nM) GLS inhibitors identified from the aforementioned medicinal chemistry efforts will be evaluated for nanoparticle encapsulation.

Figure 13C:
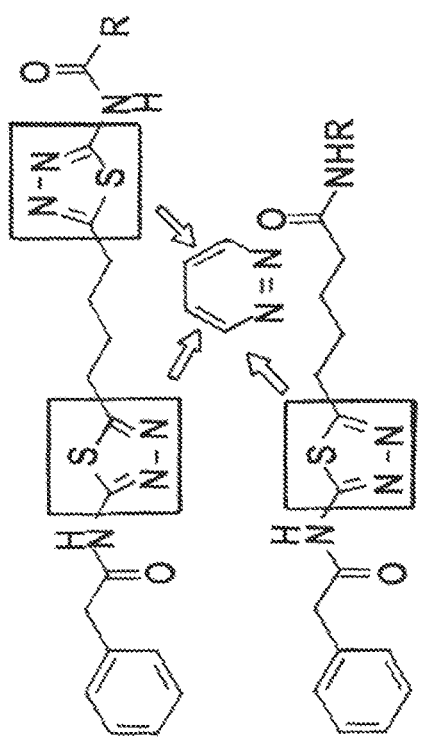

Nearly 100 compounds were synthesized throughout the course of the project and 10-20 potent GLS inhibitors ($IC_{50} \leq 300$ nM) were identified and advanced to Aim 2. If none of these new compounds show nanoparticle compatibility superior to BPTES, the structural diversity can be increased by incorporating a pyridazine ring (Scheme 3, FIG. 13C), which has previously been confirmed to serve as a replacement for the thiadiazole ring of BPTES-type GLS inhibitors.

Structures of representative compounds and $IC_{50}$'s are shown in Tables 1 and 2. Results from the initial medicinal chemistry efforts on BPTES analogs are summarized in Table 1. Compound 1 revealed that the inhibitory potency of BPTES can be retained after removal of one phenylacetyl group. However, a significant loss of potency was observed when the second phenylacetyl group was removed, as demonstrated by compound 2. Elimination of the sulfide group from compound 1 was well tolerated, as exemplified by compound 3. This finding is important since compound 2 was found to be metabolically unstable due to the oxidation of the sulfide moiety. In compound 4, the terminal aminothiadiazole ring was replaced with a secondary amide, presenting a new scaffold for GLS inhibitors.

While the findings from the initial structure activity relationship (SAR) studies of BPTES analogs provide valuable insights, there was no significant improvement in GLS inhibitory potency. Recently, however, two independent groups published crystal structures of GLS in complex with BPTES. Careful analysis of the co-crystal structure of GLS1-BPTES complex (FIG. 5) revealed that the terminal phenylacetyl groups of BPTES do not form any notable interactions with the binding site of the enzyme. A closer investigation of the co-crystal structure identified Glu325 and Arg317 in the vicinity of the phenylacetyl group. It was hypothesized that more potent GLS inhibitors can be identified by exploiting these residues for additional interactions A new structural optimization strategy built upon the GLS-BPTES co-crystal structures revealed that incorporation of a hydrogen donor moiety (such as a phenol or carboxylate group) greatly increased inhibitory potency as demonstrated by compounds 5-7 (Table 2). These results are in good agreement with the hypothesis that the Arg317 residue of GLS can be exploited for enhancement of affinity. Docking studies using the most potent inhibitor 5 (FIG. 6) also displayed putative interactions between the phenol moiety of 5 and the Arg317/Glu325 residues, further providing support for the core hypothesis. Given the importance of preserving the lipophilicity of BPTES (to enable nano-encapsulation), further structural optimization efforts will be

TABLE 1

Inhibition of GLS by BPTES analogs

| | Structure | $IC_{50}$ (μM) |
|---|---|---|
| BPTES | [structure: phenyl-CH2-C(=O)-NH-thiadiazole-CH2CH2-S-CH2CH2-thiadiazole-NH-C(=O)-CH2-phenyl] | 3.3 |
| 1 | [structure: phenyl-CH2-C(=O)-NH-thiadiazole-CH2CH2-S-CH2CH2-thiadiazole-NH2] | 2.7 |
| 2 | [structure: H2N-thiadiazole-CH2CH2-S-CH2CH2-thiadiazole-NH2] | 100 |
| 3 | [structure: phenyl-CH2-C(=O)-NH-thiadiazole-(CH2)4-thiadiazole-NH2] | 1.9 |
| 4 | [structure: phenyl-CH2-C(=O)-NH-thiadiazole-(CH2)3-C(=O)-NH-CH2CH2-pyrrolidine] | 4.6 | primarily focused on analogs of compound 5, which possesses c Log P value similar to that of BPTES.

TABLE 2

BPTES analogs with hydrogen donor moieties improve GLS inhibitory potency by >30-fold

| | Structure | IC$_{50}$ (µM) | cLogP |
|---|---|---|---|
| BPTES | 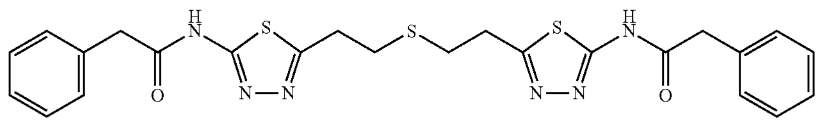 [SMILES: O=C(Cc1ccccc1)Nc1nnc(CCSCCc2nnc(NC(=O)Cc3ccccc3)s2)s1] | 3.3 | 4.2 |
| 5 | 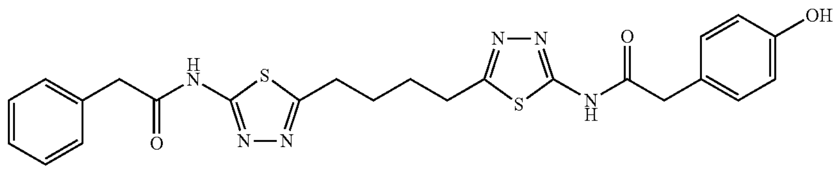 [SMILES: O=C(Cc1ccccc1)Nc1nnc(CCCCc2nnc(NC(=O)Cc3ccc(O)cc3)s2)s1] | 0.08 | 3.9 |
| 6 | 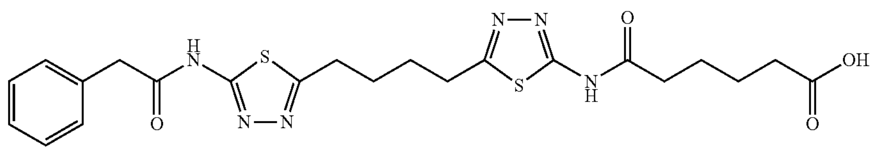 [SMILES: O=C(O)CCCCC(=O)Nc1nnc(CCCCc2nnc(NC(=O)Cc3ccccc3)s2)s1] | 0.1 | 3.1 |
| 7 | 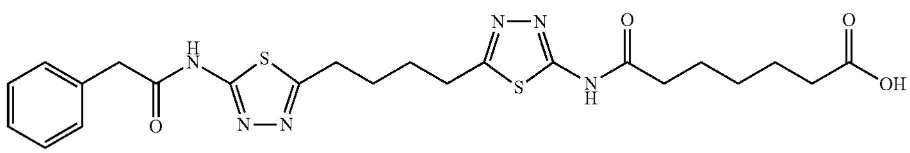 [SMILES: O=C(O)CCCCCC(=O)Nc1nnc(CCCCc2nnc(NC(=O)Cc3ccccc3)s2)s1] | 0.1 | 3.5 |

Figure 7:
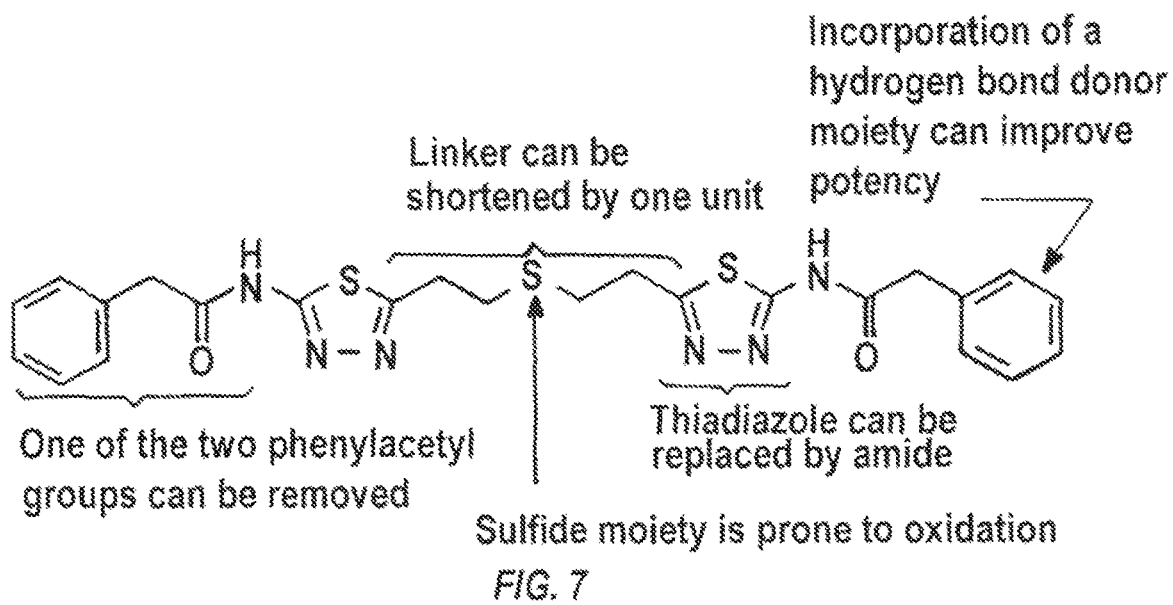
FIG. 7 is a summary schematic of PBTES analog modifications that preserve binding and inhibitory activity.

Cumulative findings from the SAR studies on BPTES analogs are summarized in FIG. 7. With respect to crystal structure, it has been possible to improve potency over 30-fold compared to BPTES, identifying analogs with IC50 values of <100 nM.

Example 3: Nanoencapsulation of GLS Inhibitors

Materials and Methods

Nanoparticles up to ~114 nm in diameter are capable of rapid penetration in rodent and human solid tumor tissue, but only if the nanoparticles are coated with an extremely dense PEG corona. Studies were conducted to determine if nanoparticles with or without dense PEG coatings remain immobilized at the injection site in the tumor following administration regardless of nanoparticle size (they are located along the needle tract only). The densely PEG-coated nanoparticles can be used to encapsulate many different drugs with high drug loadings, including BPTES.

Figure 8A:
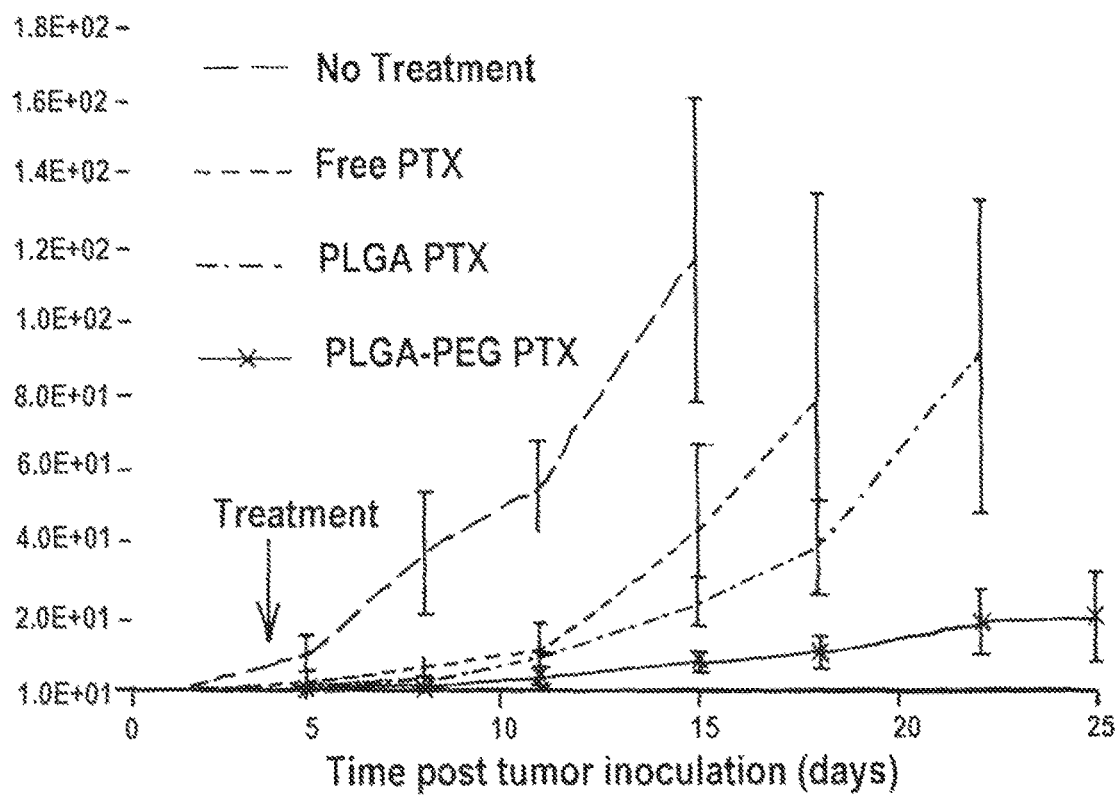
FIG. 8A is a graph showing that improved penetration of a paclitaxel-loaded PLGA-PEG nanoparticle within a tumor leads to significant tumor growth delay compared to a conventional, non-penetrating paclitaxel-loaded PLGA particle.
Figure 8B:
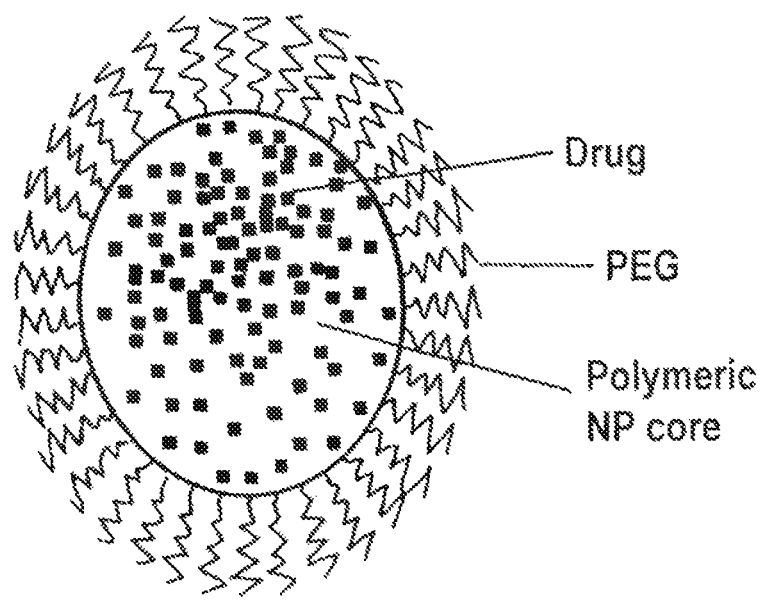
FIG. 8B is a schematic of drug loaded, densely PEGylated PLGA 60 nm nanoparticles made using emulsification method.

BPTES and its analogs are lipophilic, thus enabling the encapsulation of these drugs at high levels into biodegradable nanoparticles composed of block copolymers of poly (lactic-co-glycolic acid) and poly(ethylene glycol), or PLGA-PEG, using emulsification to prepare biodegradable PLGA-PEG nanoparticles with both dense PEG coatings and high drug loading, and sustained drug release kinetics. The emulsification method uses small molecular weight emulsifiers along with blends of PLGA and PLGA-PEG polymers that together yields nanoparticles with sub-100 nm diameters, extremely dense PEG coatings, and high drug loading (schematically depicted in FIG. 8B). These nanoparticles have been shown to be long-circulating in the blood, able to accumulate in tumors by the EPR effect, and capable of rapid penetration into brain tumors. It is expected that these nanoparticles will have similarly widespread distribution in solid pancreatic tumors.

Figure 9:
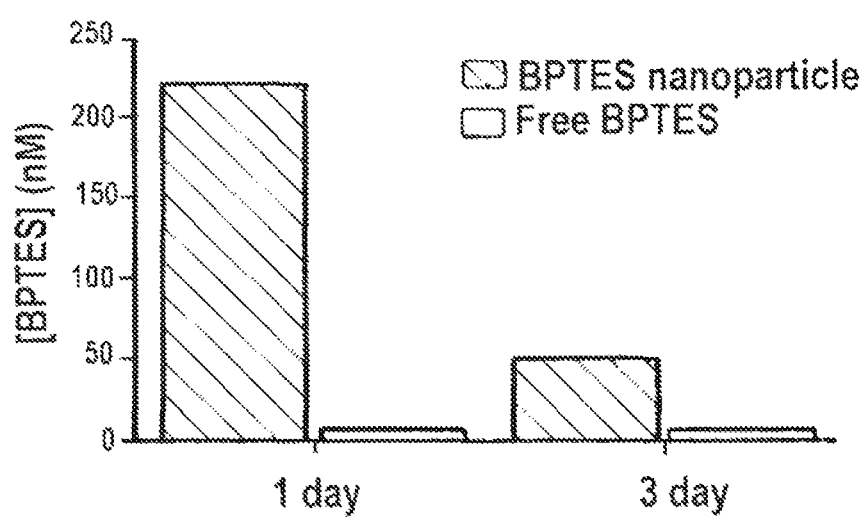
FIG. 9 is a graph of a glutamine-dependent JHU094 pancreatic patient tumor sample treated with nanoparticle encapsulated BPTES, showing nanoparticle encapsulated drug attenuated tumor growth while free GLS inhibitor treatment had no statistical benefit.

The emulsification method was used to formulate 100 nm BPTES-loaded PLGA-PEG nanoparticles with drug loading of 13% (w/w) and near neutral surface charge (~−2 mV). However, BPTES has poor aqueous solubility (<10 µg/mL) at any pH, posing a dose limiting obstacle in animals. BPTES was encapsulated in PLGA-PEG nanoparticles in order to increase drug concentration in tumors following systemic administration, as shown in FIG. 9. This schematic of drug loaded, densely PEGylated PLGA nanoparticle was made using an emulsification method. Densely PEG-coated 60 nm nanoparticles avoid reticuloendothelial system clearance and circulate at least 24 hours longer than non-PEG coated 50 nm nanoparticles, which accumulate in the liver.

Results

The non-pegylated nanoparticles did not penetrate and remain situation.

Testing in orthotopically inoculated rat tumors showed dense PEG coating significantly increased nanoparticle penetration for both PS-PEG nanoparticles and PLGA-PEG nanoparticles compared to nanoparticles without dense PEG coatings.

Improved penetration of a paclitaxel-loaded PLGA-PEG nanoparticle within a tumor can lead to significant tumor growth delay compared to a conventional, non-penetrating paclitaxel loaded PLGA particle (FIG. 8) (nanoparticle formulations otherwise identical, including drug loading level and release kinetics).

In vivo distribution of PLGA-PEG, and unmodified PLGA, nanoparticles following injection into orthotopically-implanted rodent malignant glioma show that the PEG-coated nanoparticles penetrate tumors much more effectively than uncoated standard particles. Orthotopically implanted 9 L glioma tumor in rats express bioluminescence post inoculation, which correlates to tumor growth over time.

Example 4: Testing of Nanoencapsulated BPTES for Efficacy Against Pancreatic Tumor Cells Materials and Methods Treatments were given intratumorally 4 days after tumor inoculation. Nanoparticulate paclitaxel or PBTES was administered as described in Example 3.

Results

Paclitaxel (PTX) loaded PLGA-PEG nanoparticles significantly delayed tumor growth compared to the no treatment (NT), Free PTX, and PTX loaded, non-penetrating PLGA particles of similar size and PTX loading (PLGA PTX). Preliminary data support this hypothesis.

BPTES nanoparticle delivers high BPTES levels in tumors up to 3 days post intravenous nanoparticle administration in vivo. BPTES administered as free intravenous administered drug is below the limit of detection (10 nM) in all tumor samples at all time points tested. BPTES levels were quantified by LC-MS/MS.

Significant BPTES concentrations were found in pancreatic tumors in mice even 3 days post intravenous injection, whereas the level of BPTES was undetectable at all time points when BPTES was given as free drug at the highest level possible (see below—dose limited by solubility and injection volume).

The encapsulation of BPTES into nanoparticles enabled an increase in the amount of BPTES that could be IV injected (1.2 mg in 100 µl single dose). In comparison, one could inject only 0.3125 mg free BPTES in 100 µl. DMSO solution per dose, as this was is the highest dose that could be administered based on solubility and injection volume limitations.

Figure 10A:
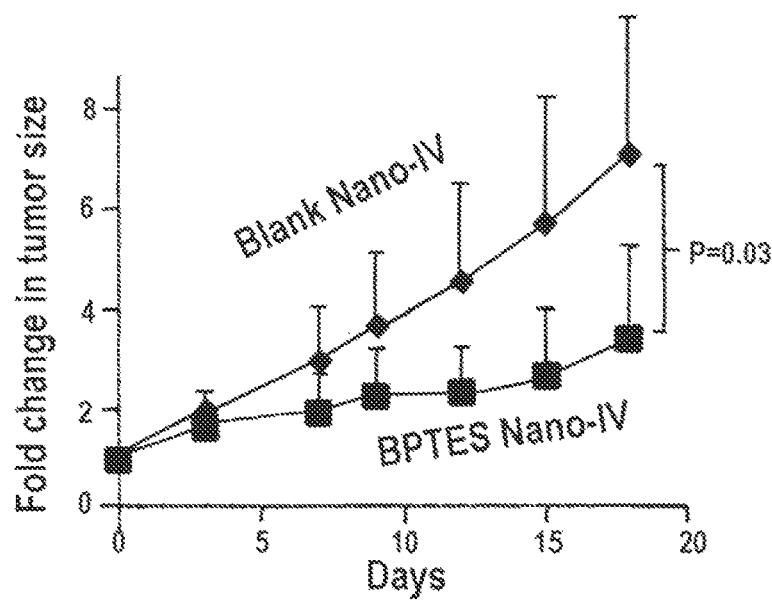
FIGS. 10A and 10B are graphs showing fold change in tumor sizes after treatment with blank nanoparticles or BPTES encapsulated in nanoparticles (FIG. 10A); fold change in tumor sizes after treatment with vehicle control or free BPTES in a JHU094 tumor (FIG. 10B). Change in tumor volume ($mm^3$) of human pancreatic cancer after treatment with 0.3125 mg BPTES twice per week.
Figure 10B:
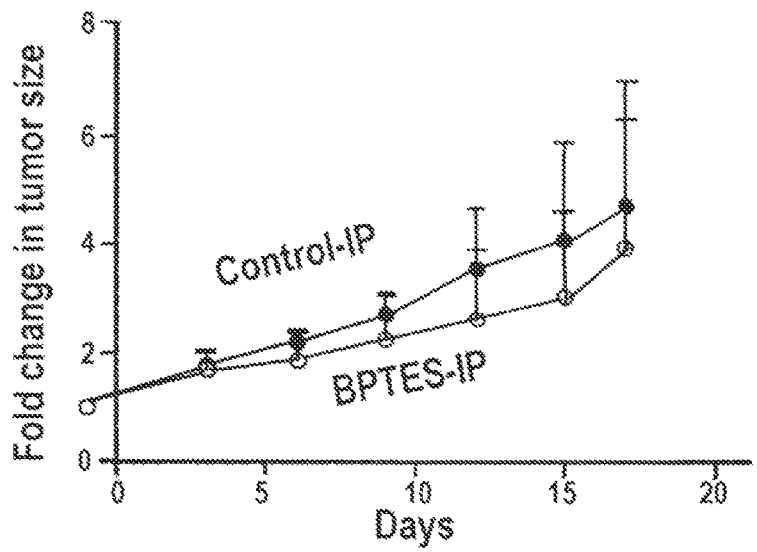
Figure 11A:
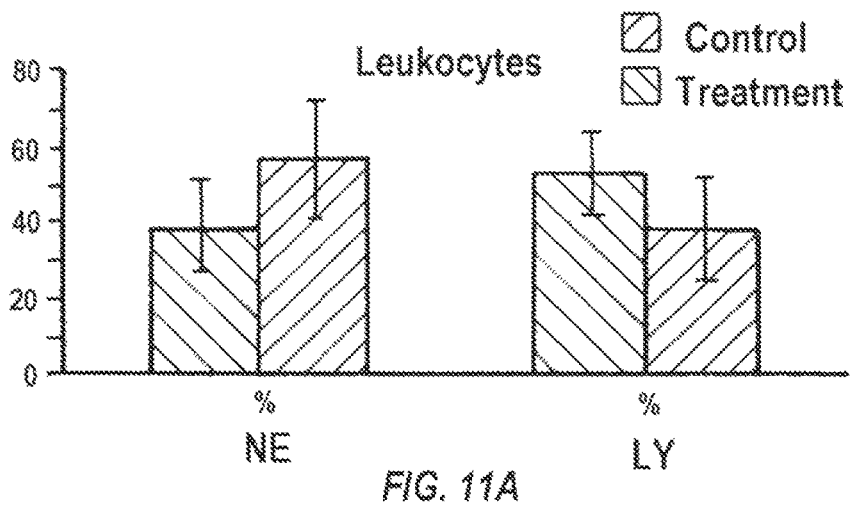
FIGS. 11A-11H are graphs showing the effect of nanoparticle encapsulated BPTES treatment on blood chemistries and hematology. Average values±SD are shown for five animals in each group. NE: neutrophils; LY: lymphocytes; MO: monocytes; EO, eosinophils; BA: basophils; RBC: red blood cells; Hb: hemoglobin; HCT: hematocrit; MCV: mean corpuscular volume; MCH: mean corpuscular hemoglobin; RDW: red cell distribution width; PLT: thrombocytes; ALT, alanine aminotransferase; AST, aspartate aminotransferase; ALB, albumin; ALP, GGT: gamma-glutamyl transferase; CAL: calcium; UA: uric acid; CREAT: creatinine; TBILI: total bilirubin; ALB: albumin; TPROT, total protein; Chol: cholesterol; HDL: high-density lipoprotein; TRIG: triglyceride; GLU, glucose; LDH: lactate dehydrogenase.
Figure 11B:
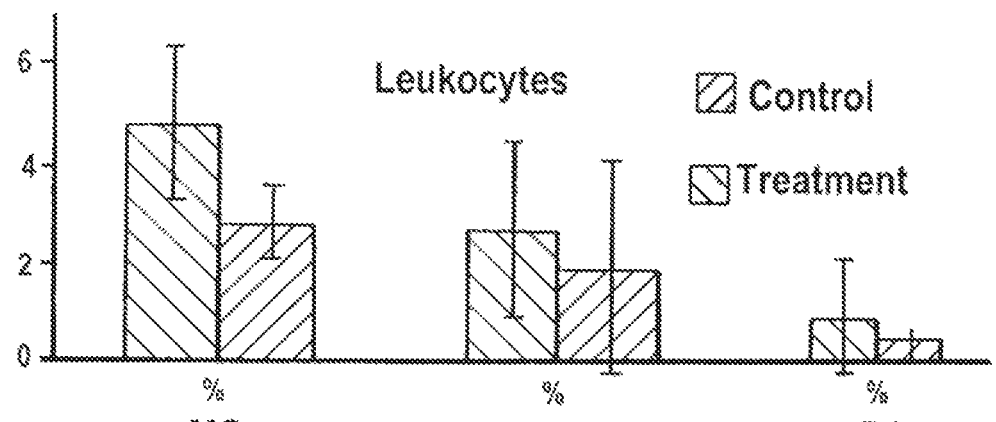
Figure 11C:
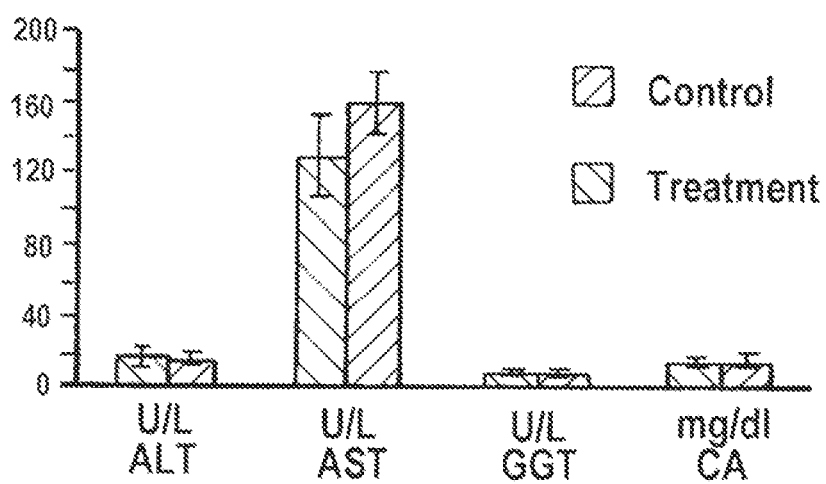
Figure 11D:
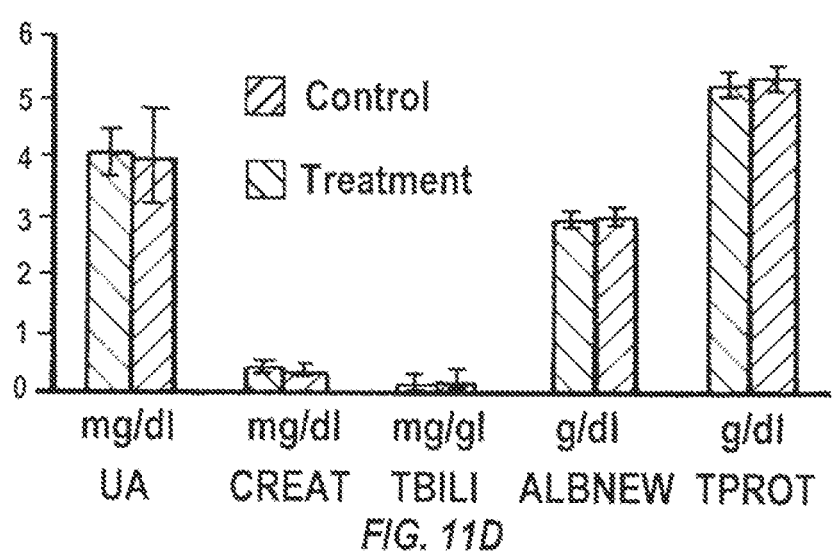
Figure 11E:
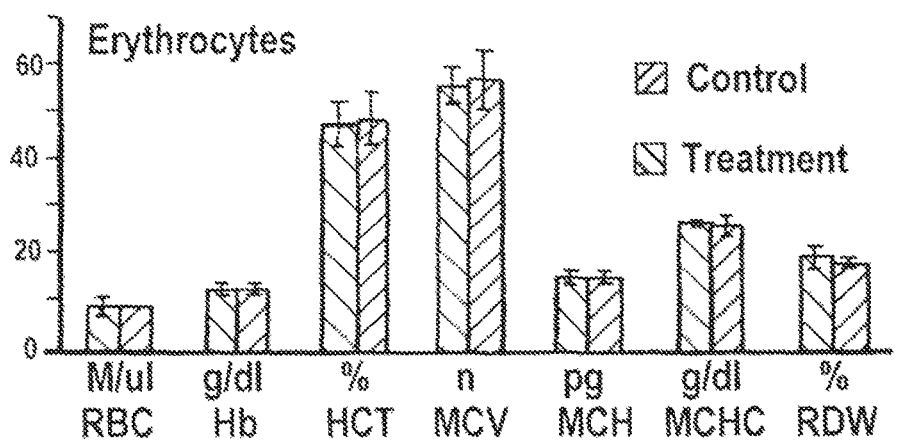
Figure 11F:
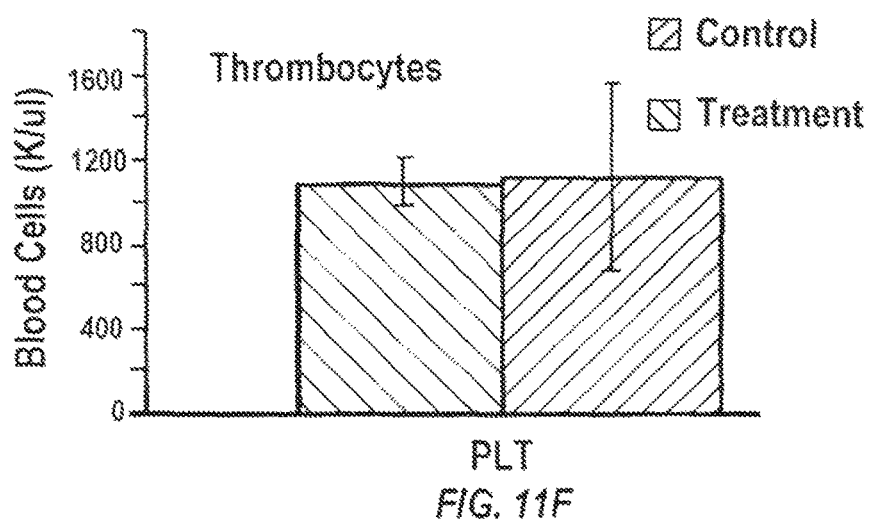
Figure 11G:
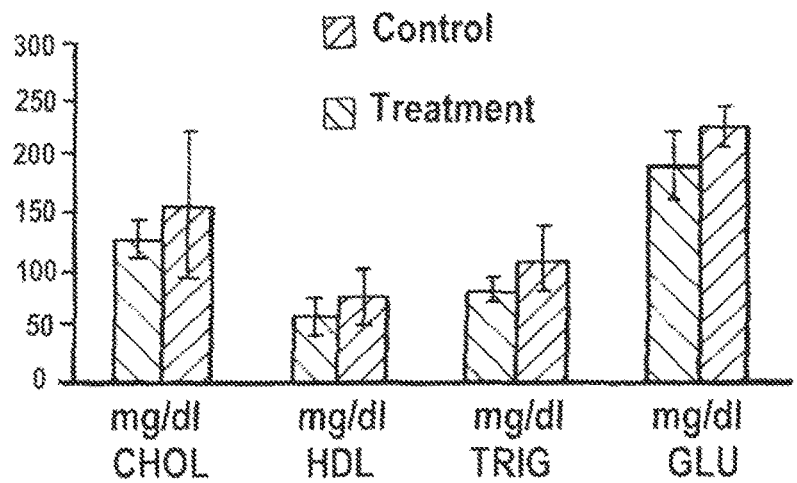
Figure 11H:
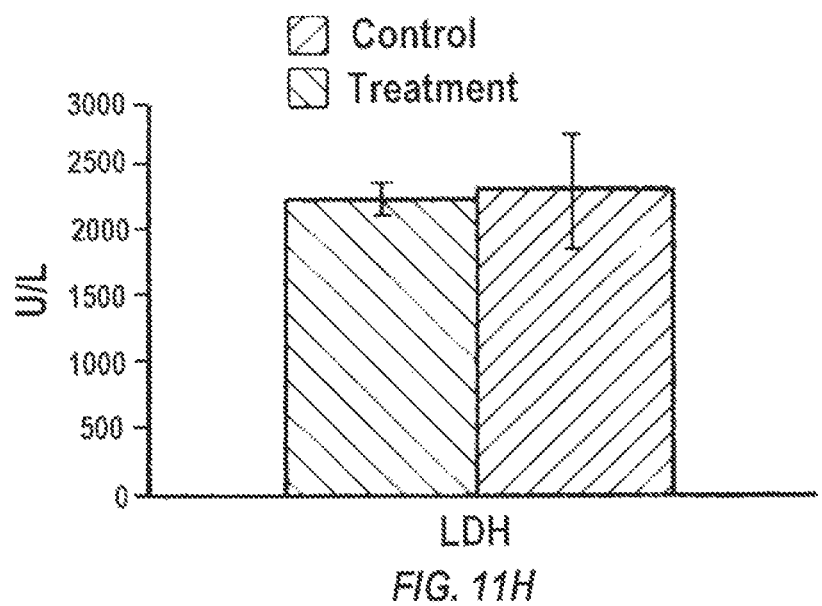

As shown in FIG. 10, using a glutamine-dependent JHU094 pancreatic patient tumor sample, it was found that the nanoparticle encapsulated BPTES attenuated tumor growth while free GLS inhibitor treatment had no statistical benefit. Animals treated with nanoparticle encapsulated BPTES did not lose weight or show signs of overt toxicity. In addition, the hematological studies did not show cytopenia, evidence of kidney [blood urea nitrogen (BUN) or creatinine] or liver (aspartate aminotransferase, alanine aminotransferase, and alkaline phosphatase) toxicity in nanoparticle treated mice as compared to the normal ranges (FIGS. 11A-11H).

The drug nanoparticle strategy for pancreatic cancer is significant. Not only can one make nanoparticles with high drug loading, sustained drug release, and long-circulation, but the extremely dense PEG coating methods allow greatly enhanced drug/particle penetration within tissues and tumors. Nanoparticle vehicles have been rationalized as an approach to circumvent the stromal barrier, which is a clinical challenge to drug delivery in pancreatic cancer. Data indicates that GLS inhibitors can be administered in higher concentrations with nanoparticles (since the nanoparticles serve to package the drug into "soluble" colloidal nanoparticles) and that nanoparticle deliver higher drug exposure selectively to the tumors due to the enhanced permeability and retention (EPR) effect. These factors result in sustained drug levels above the IC50 within the tumors for days providing significantly enhanced efficacy compared to unencapsulated drug.

Example 5: Nanoencapsulated Glutaminase Inhibitor-Chemotherapeutic Drug Combination Therapy Materials and Methods BPTES-nanoparticles have been shown to be as effective as gemcitabine at inhibiting tumor growth in patient-derived orthotopic xenografts. Patient-derived orthotopic pancreatic cancer xenografts were generated from the same patient sample, which has KRAS mutation, and treated with BPTES in nanoparticles or free gemcitabine, a current standard adjuvant chemotherapy after surgery for PDAC.

BPTES nanoparticles were injected at the dose of 1.2 mg every 3 days by intravenous administration, while 625 µg gemcitabine in 100 µl of saline was injected twice per week by intra-peritoneal administration (n=5 for each group) for 4 weeks.

Results

Figure 12A:
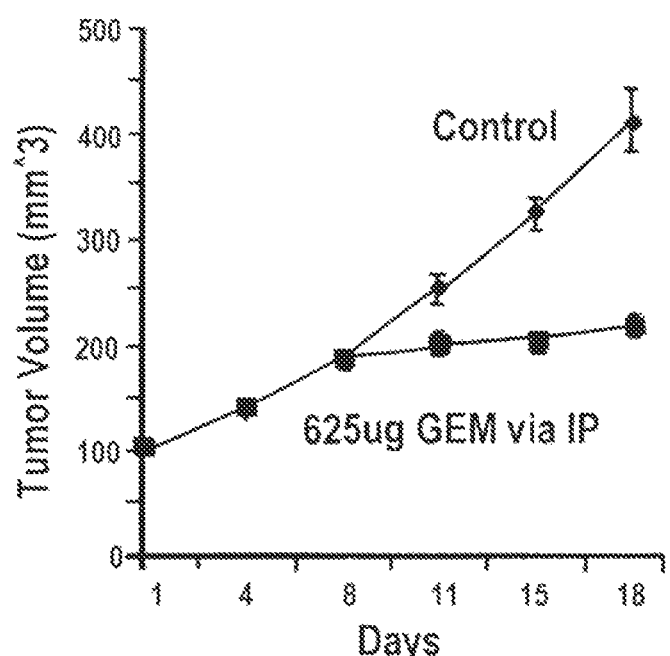
FIGS. 12A-12C are graphs showing the effect of BPTES nanoparticles and/or gemcitabine treatment on Panc265 tumor growth in vivo. BPTES nanoparticles were injected at the dose of 1.2 mg every 3 days by intravenous administration, while 625 ug gemcitabine in 100 ul of saline was injected twice per week by intra-peritoneal administration (n=5 for each group) for 4 weeks.
Figure 12B:
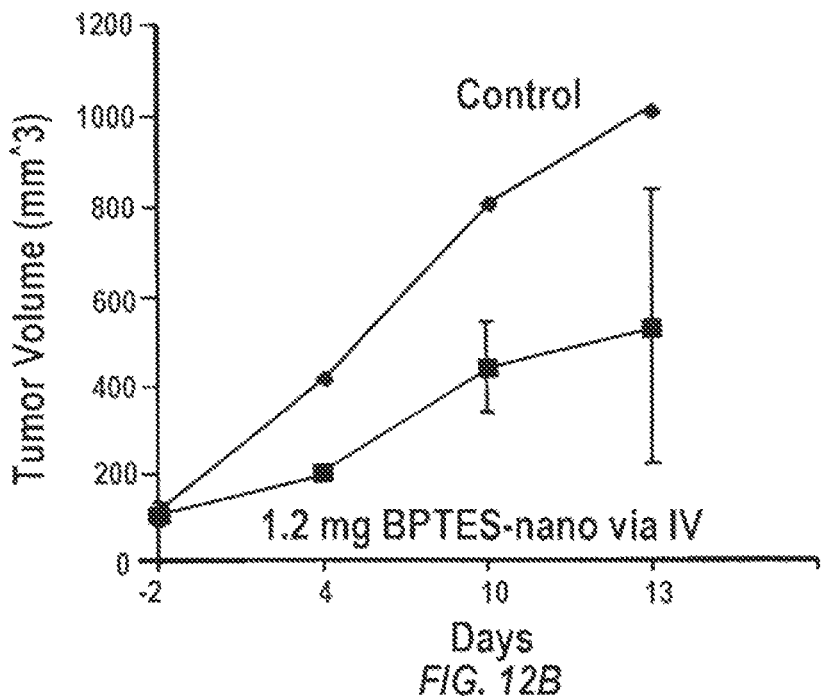
Figure 12C:
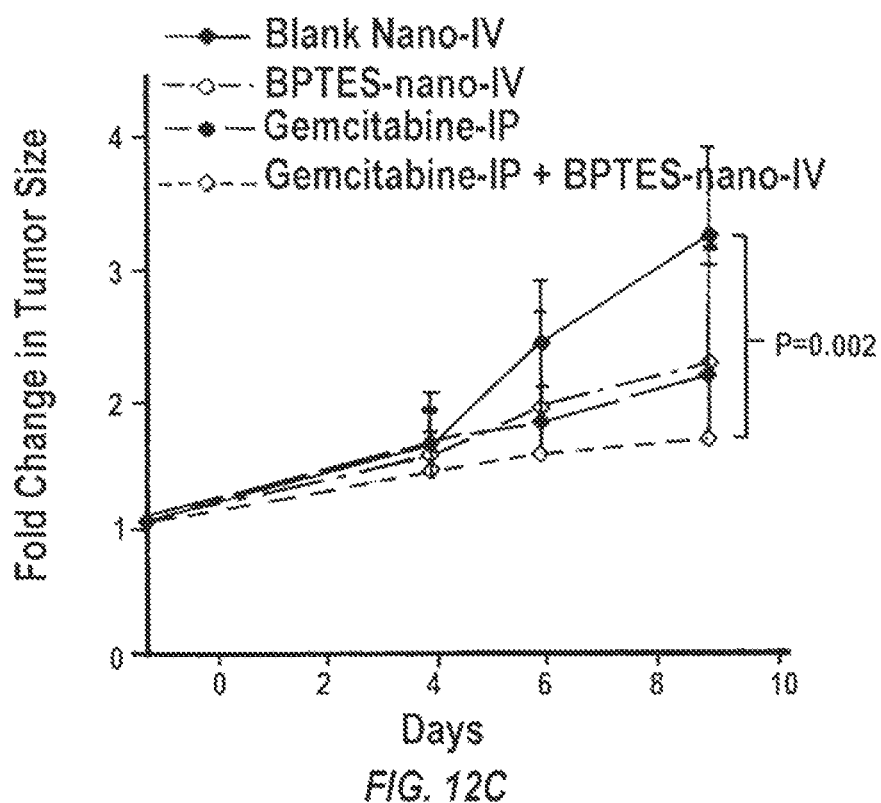

The combination resulted in greater tumor reduction. Using a dosing regimen shown to be effective for gemcitabine, treatment with either gemcitabine or BPTES-nanoparticle led to an approximately 40-50% reduction in tumor growth. Moreover, the combination of BPTES-nanoparticle and gemcitabine resulted in even greater tumor reduction (FIG. 12A-12C), showing the effect of BPTES nanoparticles and/or gemcitabine treatment on Panc265 tumor growth in vivo.

Example 6: Optimization of Nanoparticle Selection and Formulation

The results demonstrate that encapsulating BPTES into sub-100 nm size nanoparticles with high PEG density on surface, 13% BPTES by weight, >3 days steady release in vivo was highly efficacious. The key properties sought are summarized in Chart 1, and include: (i) nanoparticle size ≤100 nm (to reduce removal by the RES, enhance accumulation in tumors by the EPR effect, and enhance penetration within tumors to provide a more uniform tumor drug concentration), (ii) PEG surface density with $[\Gamma/SA] \geq 2.0$ (where SA is the surface area of nanoparticle, and $\Gamma$ is the total surface area coverage that would be provided by the PEG molecules assuming that PEG conformation on the particle surface was unconstrained to reduce removal by the RES, enhance accumulation in tumors by the EPR effect, and enhance penetration within tumors to provide a more uniform tumor drug concentration), (iii) drug loading ≥5% wt/wt (to minimize required infusion time in the clinic, and (iv) in vitro drug release for ≥72 h with ≤20% initial drug burst, where "burst" is defined here as drug release within the first 6 h (to provide sustained therapeutic effect that increases efficacy).

The formulation parameters that can be varied in encapsulation to optimize each drug are summarized in Table 3.

TABLE 3

Formulation parameters for development of an optimal nanoparticle platform

| Parameter to be Varied | Range (will be expanded if needed on drug-by-drug basis) |
|---|---|
| Organic solvent | DCM, DCM/Methanol, DCM/DMSO, ACN, THF |
| Emulsifier | Cholic acid, sugar ester, F-127, Tween 20, PVA |
| Emulsifier concentration (%) | 0.1%, 0.5%, 1%, 2% |
| Base Polymer Types | PLGA-PEG (L:G = 50:50), PLGA-PEG (L:G = 75:25), PLGA-PEG (L:G = 25:75) PLA-PEG |
| Blending PLGA polymer | PLGA (optimal L:G ratio determined in prescreen) with MW = 4, 10, 20 or 40 kDa |
| Blend ratio (i.e. PLGA:PLGA-PEG) | 0:100, 25:75, 50:50, 75:25, 100:0 (control) Note: 0:100 means all polymer chains have PEG) |
| PEG content (w/w %) | 0% (control), 5%, 8%, 10%, 15% (8-10% typically gives dense coating and high drug load) |
| PEG molecular weight (kDa) | 2 kDa, 5 kDa, 10 kDa |
| Total Polymer Conc. (mg/ml) | 50, 100, 200 |
| Target drug loading ratio (w/w %) | 10%, 20%, 30% |

The process of nanoparticle formulation optimization, summarized in Table 3, is typically as follows:

(i) Test solubility of the drug in various solvents to select a suitable solvent system. Most often, dichloromethane (DCM) alone is optimal for hydrophobic drugs like those being used here. However, drugs sometimes do not dissolve completely in DCM, and in these cases we test co-solvent systems such as DCM/methanol and DCM/DMSO.

(ii) Utilizing PLGA (typically starting with 50:50 ratio of lactic acid to glycolic acid, or 50:50 LA:GA) and a target loading of 10% w/w drug, screen several surfactants (at various surfactant concentrations) to determine which gives the highest drug loading. Then use this emulsifier going forward.

(iii) Once the solvent and the emulsifier have been identified, screen to select a base PLGA-PEG polymer type that gives the highest drug loading and lowest drug burst effect.

(iv) Screen a number of PLGA polymers (without PEG) as "blending polymers". Blending these polymers into the formulation leads to much higher drug loading, while still allowing high surface PEG density.

(iv) The PEG molecular weight (MW) that further improves drug loading, reduces burst, and that leads to dense PEG coatings with [Γ/SA]≥2.0, is determined. 8-10% PEG works well.

(v) The total polymer concentration, PEG weight percent and target drug:polymer ratio are optimized in order to fine tune particle size, PEG surface density, drug loading level, and drug release kinetics including initial burst. The nanoparticle formulations are as outlined in Table 4. The impact of PEG on biodegradable polymeric nanoparticles is dependent on PEG molecular weight, particle core material, and PEG weight percent, and that high density coatings of PEG with MW ranging from 2 k to 10 k is optimal to achieve stealth properties. Applied NMR is used to quantify the surface PEG density on nanoparticles and determine PEG conformation. Based on the surface PEG density quantification, diffusive NP behavior in tumor tissue (both rodents and human) with 100 nm particles that possess PEG corona where PEG conformation is in the dense brush regime: Γ/SA≥2.0 (this correlates to about 9 PEG/nm2 for PEG5 kDa), whereas Γ/SA≤1.7 was insufficient. PEG conformation on 100-nm particles with PEG at Γ/SA≥2.0 penetrate rapidly through tumor tissues, leading to more effective tumor control expect to develop sub-100 nm BPTES- and BPTES-analog encapsulated nanoparticles with dense PEG coating, high drug loading, and capable of sustained drug release. The dense coating of PEG and sub-100 nm particle size will lead to enhanced systemic circulation, tumor accumulation, and penetration into solid tumor. BPTES analogs will be designed to have properties that make them similarly amenable to nanoencapsulation (this consideration is a strength of the proposal as it is rare that drug discovery is done with nanoencapsulation amenability as a criteria), there are many formulation parameters available for fine adjustment, and we have deep expertise in nanoparticle formulation for drug delivery to tumors. Inevitably, some BPTES-analog drugs with high potency will be difficult to incorporate into nanoparticles that meet our strict criteria.

We claim:

1. A compound selected from the group of compounds having the structure:

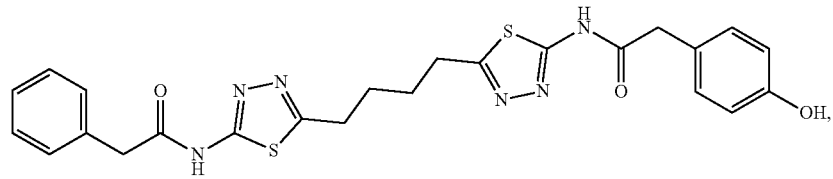

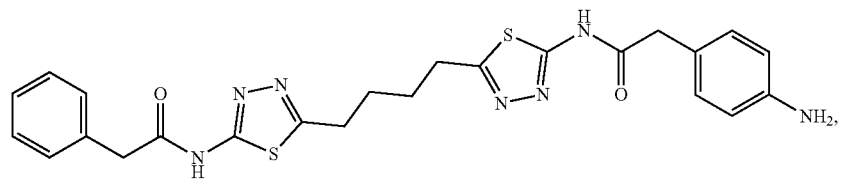

-continued
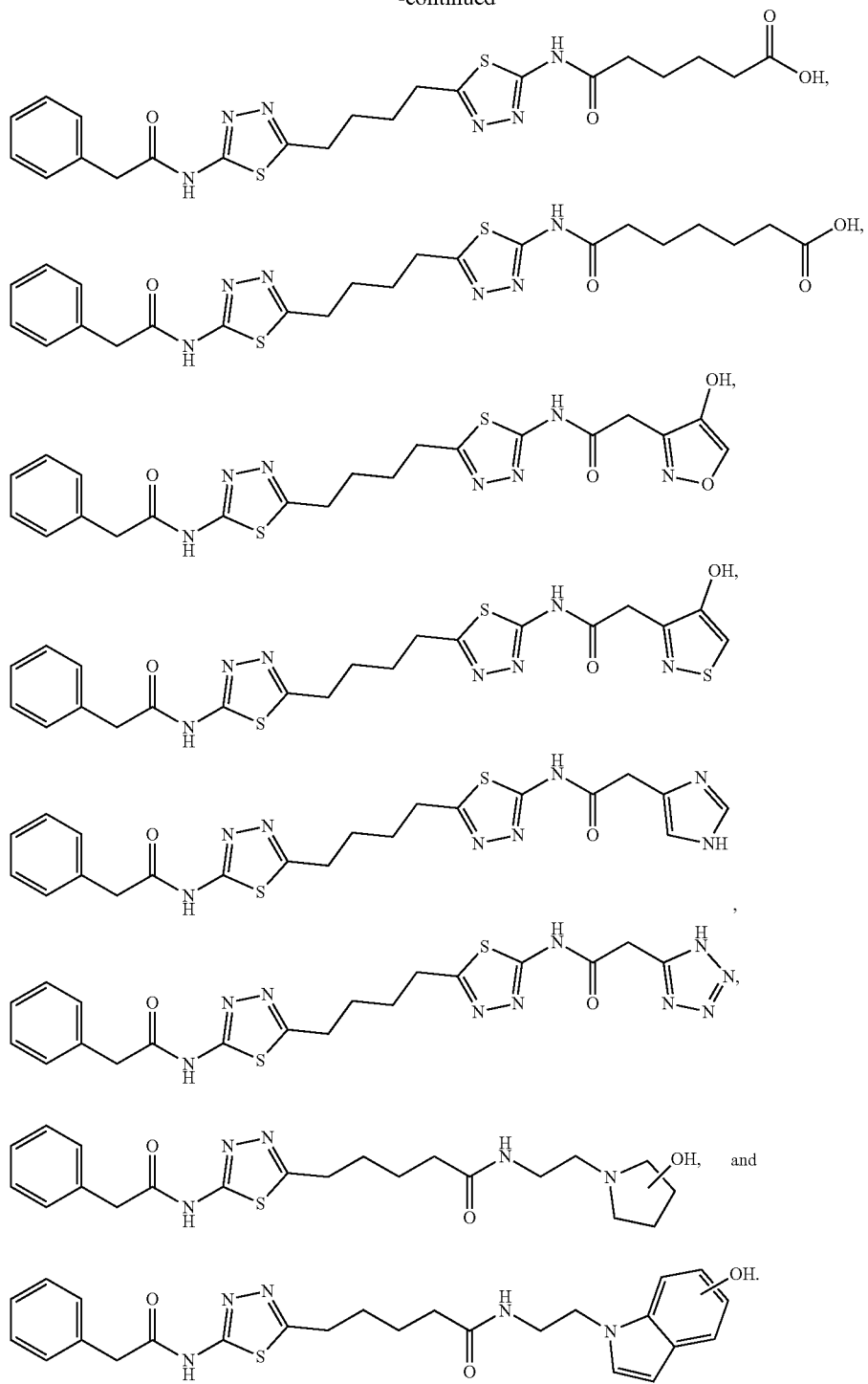
2. The compound of claim 1 having the structure
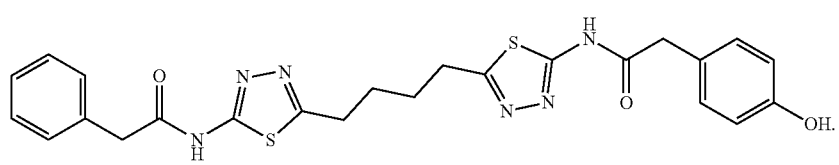 [SMILES: O=C(Cc1ccccc1)Nc1nnc(CCCCc2nnc(NC(=O)Cc3ccc(O)cc3)s2)s1]

3. The compound of claim 1 having the structure
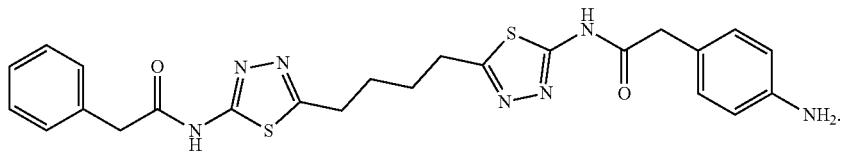 [SMILES: Nc1ccc(CC(=O)Nc2nnc(CCCCc3nnc(NC(=O)Cc4ccccc4)s3)s2)cc1]
4. The compound of claim 1 having the structure
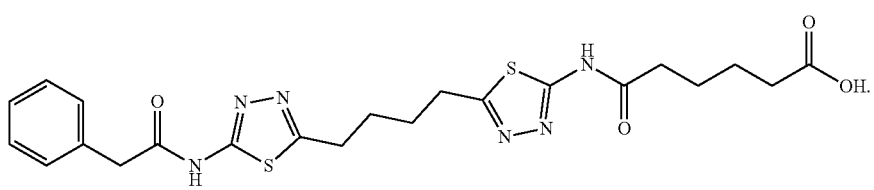 [SMILES: O=C(O)CCCCC(=O)Nc1nnc(CCCCc2nnc(NC(=O)Cc3ccccc3)s2)s1]
5. The compound of claim 1 having the structure
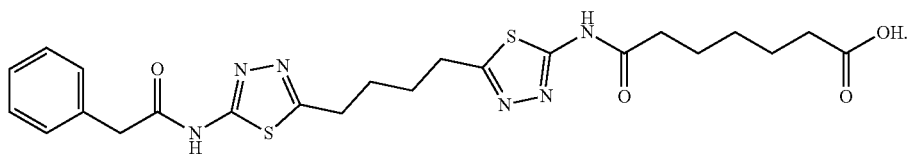 [SMILES: O=C(O)CCCCCC(=O)Nc1nnc(CCCCc2nnc(NC(=O)Cc3ccccc3)s2)s1]
6. The compound of claim 1 having the structure
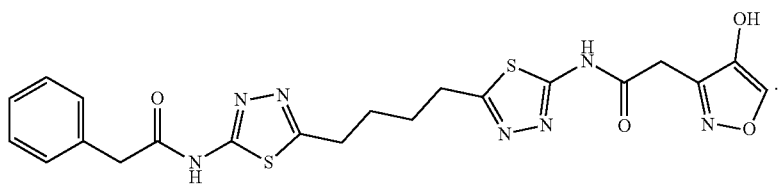 [SMILES: O=C(Cc1ccccc1)Nc1nnc(CCCCc2nnc(NC(=O)Cc3nocc3O)s2)s1]
7. The compound of claim 1 having the structure
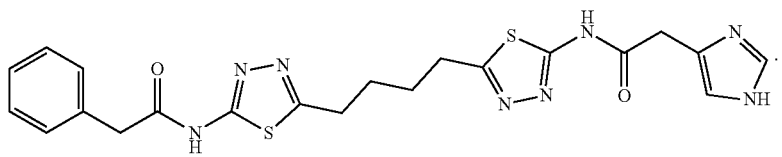 [SMILES: O=C(Cc1ccccc1)Nc1nnc(CCCCc2nnc(NC(=O)Cc3c[nH]cn3)s2)s1]
8. The compound of claim 1 having the structure
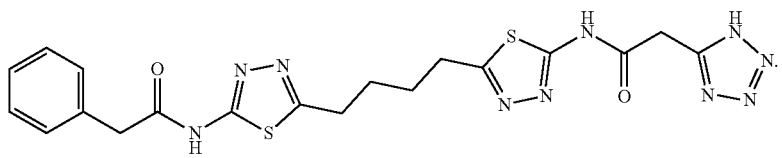 [SMILES: O=C(Cc1ccccc1)Nc1nnc(CCCCc2nnc(NC(=O)Cc3nnn[nH]3)s2)s1]

9. The compound of claim 1 having the structure
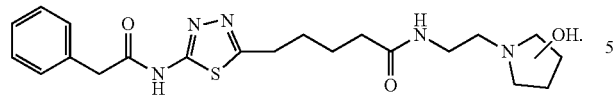
10. The compound of claim 1 having the structure
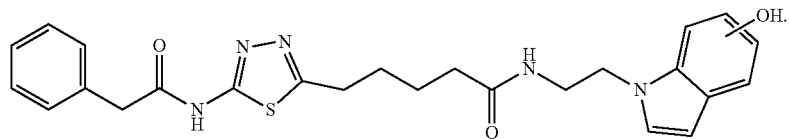
11. The compound of claim 1 having the structure
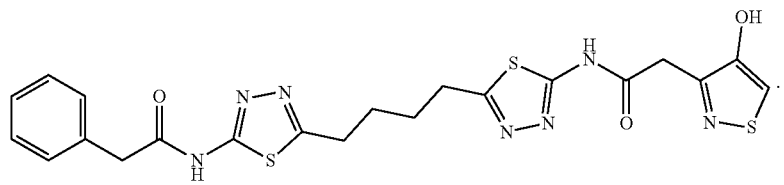 [SMILES: O=C(Cc1ccccc1)Nc1nnc(CCCCc2nnc(NC(=O)Cc3nscc3O)s2)s1]
* * * * *